United States Patent
Varvel et al.

(10) Patent No.: US 9,915,645 B2
(45) Date of Patent: Mar. 13, 2018

(54) METHOD OF TREATING A PATIENT DETERMINED TO BE AT RISK OF DEVELOPING OCCULT PANCREATIC BETA-CELL DYSFUNCTION

(71) Applicant: True Health Diagnostics, LLC, Frisco, TX (US)

(72) Inventors: Steve Varvel, Richmond, VA (US); Rebecca E. Caffrey, N. Chesterfield, VA (US); James V. Pottala, Sioux Falls, SD (US)

(73) Assignee: True Health IP LLC, Frisco, TX (US)

( * ) Notice: Subject to any disclaimer, the term of this patent is extended or adjusted under 35 U.S.C. 154(b) by 0 days.

(21) Appl. No.: 14/153,994

(22) Filed: Jan. 13, 2014

(65) Prior Publication Data

US 2014/0200177 A1 Jul. 17, 2014

Related U.S. Application Data

(60) Provisional application No. 61/751,328, filed on Jan. 11, 2013, provisional application No. 61/831,337, filed on Jun. 5, 2013, provisional application No. 61/831,405, filed on Jun. 5, 2013.

(51) Int. Cl.
*A61K 38/00* (2006.01)
*G01N 33/50* (2006.01)
*G01N 33/92* (2006.01)

(52) U.S. Cl.
CPC ............. *G01N 33/50* (2013.01); *G01N 33/92* (2013.01); *G01N 2800/042* (2013.01); *G01N 2800/044* (2013.01); *G01N 2800/50* (2013.01)

(58) Field of Classification Search
CPC ..... G01N 2800/04; A61K 31/64; A61K 38/28
See application file for complete search history.

(56) References Cited

U.S. PATENT DOCUMENTS

2015/0065460 A1* 3/2015 Gall et al. ...................... 514/77

FOREIGN PATENT DOCUMENTS

| WO | 2010114897 A1 | 10/2010 |
|---|---|---|
| WO | 2013039898 A1 | 3/2013 |

OTHER PUBLICATIONS

Joffe et al., Diabetes in Control, News and Information for medical Professional, Sep. 27, 2011.*
Bonora et al., Nutr. Metab. and Cardiovasc. Diseases, 18: 74-83, 2008.*
Raz et al., Diabetes Care, 36:S190-S197, 2013.*
Abdul-Ghani et al., "Plasma Glucose Concentration and Prediction of Future Risk of Type 2 Diabetes," Diabetes Care 32(Suppl. 2): S194-S198 (2009).
Ferrannini et al., "Early Metabolic Markers of the Development of Dysglycemia and Type 2 Diabetes and Their Physiological Significance," Diabetes 62: 1730-1737 (2013).
Gall et al., "α-Hydroxybutyrate Is an Early Biomarker of Insulin Resistance and Glucose Intolerance in a Nondiabetic Population," Plos One 5(5): e10883 (2010).
Dungan et al., "1,5-Anhydroglucitol and Postprandial Hyperglycemia as Measured by Continuous Glucose Monitoring System in Moderately Controlled Patients with Diabetes," Diabetes Care 29(6): 1214-1219 (2006).
International Search Report and Written Opinion dated Mar. 18, 2014 for International Application No. PCT/US14/11340.
Atkinson et al., "Type 1 Diabetes: New Perspectives on Disease Pathogenesis and Treatment," The Lancet, 358 (9277):221-229 (2001).
International Search Report dated Mar. 27, 2014 for International Application No. PCT/US14/11335.
"Report of the Expert Committee on the Diagnosis and Classification of Diabetes Mellitus," Diabetes Care, 20(7):1183-1197 (1997).

* cited by examiner

*Primary Examiner* — Gyan Chandra
(74) *Attorney, Agent, or Firm* — Perkins Coie LLP

(57) ABSTRACT

This invention relates to a method for detecting the presence of or likelihood of a patient of developing occult pancreatic beta cell dysfunction, and a method for detecting the presence of or likelihood of a patient of developing clinically significant post-prandial hyperglycemia. The methods involve (a) measuring a level of alpha-hydroxybutyrate (AHB) in a single fasting baseline biological sample of the patient; (b) comparing the level of AHB in the single fasting baseline biological sample to a reference AHB level; and (c) determining the presence of or likelihood of developing the disorder in the patient based on the comparison in step (b). An increased AHB level at fasting baseline indicates that a normoglycemic, normo-insulinemic and/or non-dyslipidemic patient has developed or has an increased likelihood of developing occult pancreatic beta cell dysfunction. An increased AHB level at fasting baseline and an elevated glucose level of at least about 155 mg/dL at 30 minutes and/or 1 hour indicates that a normoglycemic, normo-insulinemic and/or non-dyslipidemic patient has developed or has an increased likelihood of developing clinically significant post-prandial hyperglycemia.

21 Claims, 24 Drawing Sheets

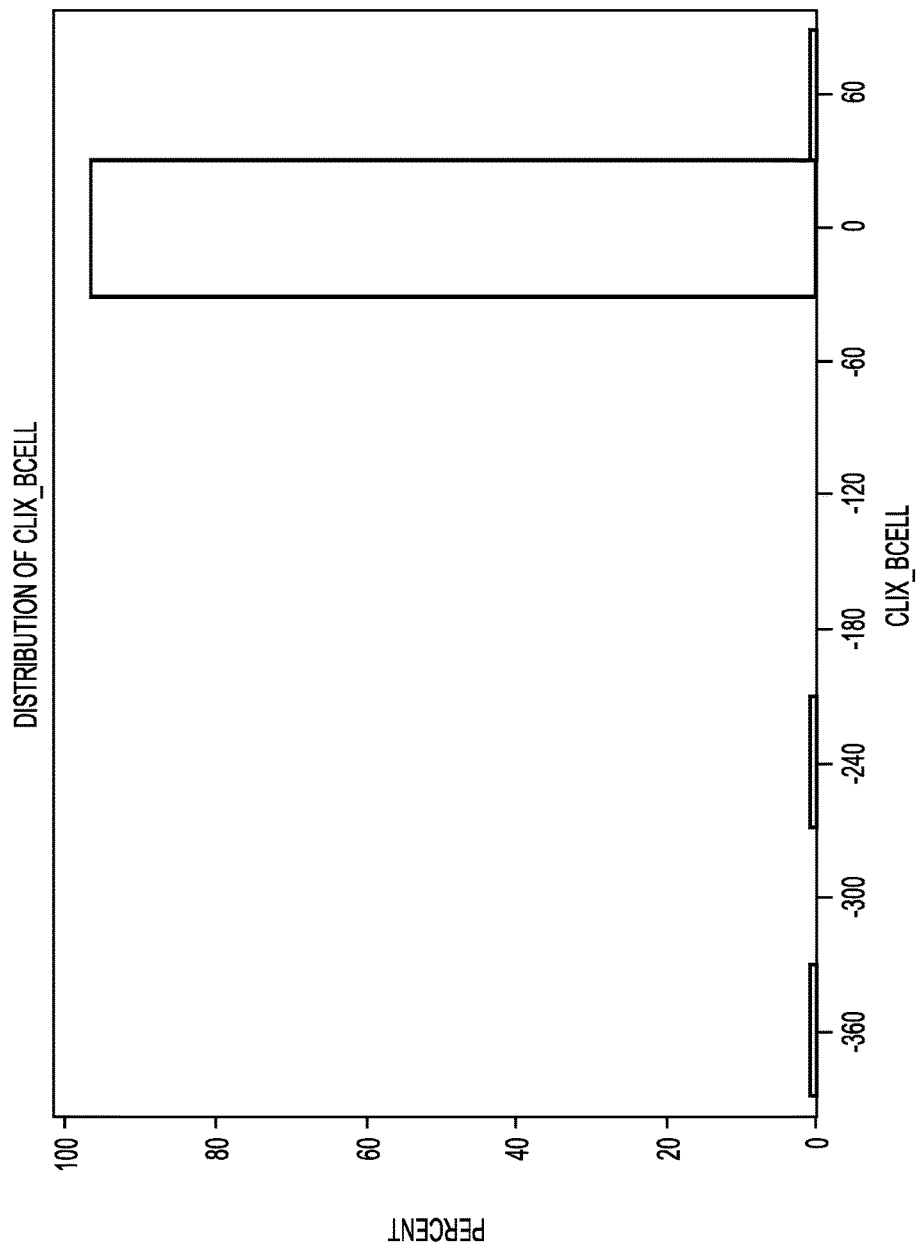

FIG. 16A

| LABORATORY TEST | NOTES | HIGH RISK | INTERMEDIATE RISK | OPTIMAL | HIGH RISK RANGE | INTERMEDIATE RISK RANGE | OPTIMAL RANGE | PREVIOUS RESULTS 2/8/2012 |
|---|---|---|---|---|---|---|---|---|
| TOTAL CHOLESTEROL (mg/dL) | | | | | ≥240 | 200 - 239 | <200 | |
| LDL-C DIRECT (mg/dL) | | | | | ≥130 CHD & CHD RISK EQ. >100 | 100-129 CHD & CHD RISK EQ. 70-100 | <100 CHD & CHD RISK EQ. <70 | |
| HDL-C (mg/dL) | | | | | <40 | | ≥40 | |
| TRIGLYCERIDES (mg/dL) | | | | | >199 | 150 - 199 | <150 | |
| NON-HDL-C (mg/dL) (CALCULATED) | | | | | ≥160 | 130 - 159 | <130 | |

FIG. 16B

| LABORATORY TEST | NOTES | HIGH RISK | INTERMEDIATE RISK | OPTIMAL | HIGH RISK RANGE | INTERMEDIATE RISK RANGE | OPTIMAL RANGE | PREVIOUS RESULTS 5/2/2012 |
|---|---|---|---|---|---|---|---|---|
| TOTAL CHOLESTEROL (mg/dL) | | | | 165 | ≥240 | 200 - 239 | <200 | 193 |
| LDL-C DIRECT (mg/dL) | | | | 59 | ≥130 CHD & CHD RISK EQ. >100 | 100-129 CHD & CHD RISK EQ. 70-100 | <100 CHD & CHD RISK EQ. <70 | 74 |
| HDL-C (mg/dL) | | | | 90 | <40 | | ≥40 | 98 |
| TRIGLYCERIDES (mg/dL) | | | | 53 | >199 | 150 - 199 | <150 | 33 |
| NON-HDL-C (mg/dL) (CALCULATED) | | | | 75 | ≥160 | 130 - 159 | <130 | 95 |

FIG. 16C

| LABORATORY TEST | NOTES | HIGH RISK | INTERMEDIATE RISK | OPTIMAL | HIGH RISK RANGE | INTERMEDIATE RISK RANGE | OPTIMAL RANGE | PREVIOUS RESULTS 1/28/2013 |
|---|---|---|---|---|---|---|---|---|
| TOTAL CHOLESTEROL (mg/dL) | | | | 199 | ≥240 | 200 - 239 | <200 | 173 |
| LDL-C DIRECT (mg/dL) | | | | 85 | ≥130 CHD & CHD RISK EQ. >100 | 100-129 CHD & CHD RISK EQ. 70-100 | <100 CHD & CHD RISK EQ. <70 | 68 |
| HDL-C (mg/dL) | | | | 106 | <50 | | ≥50 | 96 |
| TRIGLYCERIDES (mg/dL) | | | | 61 | >199 | 150 - 199 | <150 | 39 |
| NON-HDL-C (mg/dL) (CALCULATED) | | | | 93 | ≥160 | 130 - 159 | <130 | 77 |

| | LABORATORY TEST | NOTES | HIGH RISK | INTERMEDIATE RISK | OPTIMAL | HIGH RISK RANGE | INTERMEDIATE RISK RANGE | OPTIMAL RANGE | PREVIOUS RESULTS 2/8/2012 |
|---|---|---|---|---|---|---|---|---|---|
| GLYCEMIC CONTROL | GLUCOSE (mg/dL) | | | | 96 | <55 OR >125 | 56-69 OR 100-125 | 70 - 99 | 77 |
| | HbA1c (%) | | | | 4.9 | ≥6.5 | 5.7 - 6.4 | ≤5.6 | 4.8 |
| | FRUCTOSAMINE (µmol/L) | | | | 238 | >339 | 293 - 339 | <293 | |
| | GLYCATION GAP | | | | -0.74 | >0.77 | 0.45 - 0.77 | <0.45 | |
| BETA CELL FUNCTION | INSULIN (µU/mL) | | 17 | | | ≥12 | 10 - 11 | 3 - 9 | 7 |
| | PROINSULIN (pmol/L) | | | 11 | | >16 | 8 - 16 | <8 | |
| | C-PEPTIDE (ng/mL) | | | 3.8 | | >4.6 | 3.1 - 4.6 | 1.0 - 3.0 | 3.1 |
| | ANTI-GAD (GLUTAMIC ACID DECARBOXYLASE ANTIBODY) (IU/mL) | | | | <5 | >5 POSITIVE | | ≤5 NEGATIVE | |
| INSULIN RESISTANCE | LEPTIN (ng/mL) | | | | 5 | >43 | 20 - 43 | <20 | |
| | ADIPONECTIN (µg/mL) | | | | 15 | <10 | 10 - 14 | >14 | |
| | FERRITIN (ng/mL) | | | | 16 | >108 | 61 - 108 | <61 | |
| | FREE FATTY ACID (mmol/L) | | | | 0.25 | >0.7 | 0.6 - 0.7 | <0.6 | |
| | α-HYDROXYBUTYRATE (µg/mL) | | | | 3.7 | >5.7 | 4.5 - 5.7 | <4.5 | |
| | OLEIC ACID (µg/mL) | | | | 17 | >79 | 60 - 79 | <60 | 0.31 |
| | LINOLEOYL-GPC (µg/mL) | | | 12.4 | | <10.5 | 10.5 - 13.0 | >13.0 | |
| | IR SCORE | | | | 10.2 | <5.5 | 5.5 - 6.5 | >6.5 | |
| | HOMA-IR | | | 4.1 | | >4.2 | 2.6 - 4.2 | <2.6 | |

*FIG. 17A*

| | LABORATORY TEST | NOTES | HIGH RISK | INTERMEDIATE RISK | OPTIMAL | HIGH RISK RANGE | INTERMEDIATE RISK RANGE | OPTIMAL RANGE | PREVIOUS RESULTS 5/2/2012 |
|---|---|---|---|---|---|---|---|---|---|
| GLYCEMIC CONTROL | GLUCOSE (mg/dL) | | | 69 | | ≤55 OR >125 | 56-69 OR 100-125 | 70-99 | 85 |
| | HbA1c (%) | | | | 4.9 | ≥6.5 | 5.7-6.4 | ≤5.6 | 4.8 |
| | FRUCTOSAMINE (μmol/L) | | | | 238 | >339 | 293-339 | <293 | 255 |
| | GLYCATION GAP | | | | -0.74 | >0.77 | 0.45-0.77 | <0.45 | -1.16 |
| BETA CELL FUNCTION | INSULIN (μU/mL) | | | | 3 | ≥12 | 10-11 | 3-9 | 6 |
| | PROINSULIN (pmol/L) | | | | 4 | >16 | 8-16 | <8 | 5 |
| | C-PEPTIDE (ng/mL) | | | | 1.5 | >4.6 | 3.1-4.6 | 1.0-3.0 | 2.4 |
| | ANTI-GAD (GLUTAMIC ACID DECARBOXYLASE ANTIBODY) (IU/mL) | | | | <5 | >5 POSITIVE | | ≤5 NEGATIVE | <5 |
| INSULIN RESISTANCE | LEPTIN (ng/mL) | | | | 7 | >43 | 20-43 | <20 | 12 |
| | ADIPONECTIN (μg/mL) | | | | 19 | <10 | 10-14 | >14 | 15 |
| | FERRITIN (ng/mL) | | | | | >108 | 61-108 | <61 | 30 |
| | FREE FATTY ACID (mmol/L) | | | | | >0.7 | 0.6-0.7 | <0.6 | 0.52 |
| | α-HYDROXYBUTYRATE (μg/mL) | | 1.04 | | | >5.7 | 4.5-5.7 | <4.5 | 3.2 |
| | OLEIC ACID (μg/mL) | | 6.1 | | | >79 | 60-79 | <60 | 40 |
| | LINOLEOYL-GPC (μg/mL) | | 97 | | | <10.5 | 10.5-13.0 | >13.0 | 13.2 |
| | IR SCORE | | 8.3 | | 6.8 | <5.5 | 5.5-6.5 | >6.5 | 9.4 |
| | HOMA-IR | | | | 0.4 | >4.2 | 2.6-4.2 | <2.6 | 1.3 |

| | LABORATORY TEST | NOTES | HIGH RISK | INTERMEDIATE RISK | OPTIMAL | HIGH RISK RANGE | INTERMEDIATE RISK RANGE | OPTIMAL RANGE | PREVIOUS RESULTS 1/28/2013 |
|---|---|---|---|---|---|---|---|---|---|
| GLYCEMIC CONTROL | GLUCOSE (mg/dL) | | | 58 | | >125 | 100-125 | 70-99 | 88 |
| | HbA1c (%) | | | | 5.1 | ≥6.5 | 5.7-6.4 | ≤5.6 | 4.7 |
| | ESTIMATED AVERAGE GLUCOSE (mg/dL) (CALCULATED) | | | | 99.7 | ≥139.9 | 116.9-139.8 | <116.8 | 88.2 |
| | FRUCTOSAMINE (μmol/L) | | | | 233 | >339 | 293-339 | <293 | 234 |
| | GLYCATION GAP | | | | -0.44 | >0.77 | 0.45-0.77 | <0.45 | -0.86 |
| | POSTPRANDIAL GLUCOSE INDEX | | | | 5.9 | >7.9 | 6.0-7.9 | <6.0 | 6.1 |
| BETA CELL FUNCTION | INSULIN (μU/mL) | | | 16 | 5 | ≥12 | 10-11 | 3-9 | 6 |
| | PROINSULIN (pmol/L) | | 5.1 | | | >16 | 8-16 | <8 | 5 |
| | C-PEPTIDE (ng/mL) | | | 3.1 | | >4.6 | 3.1-4.6 | 1.0-3.0 | 2.1 |
| | PROINSULIN:C-PEPTIDE RATIO | | | | | >4.9 | 3.6-4.9 | <3.6 | 2.2 |
| | ANTI-GAD (IU/mL) | | | | <5 | >5 POSITIVE | | ≤5 NEGATIVE | <5 |
| INSULIN RESISTANCE | LEPTIN (ng/mL) | | | | 7 | >43 | 20-43 | <20 | 7 |
| | LEPTIN : BMI RATIO | | | | 0.38 | ≥1.17 | 0.66-1.17 | <0.66 | 0.34 |
| | ADIPONECTIN (μg/mL) | | | | 15 | <10 | 10-14 | >14 | 12 |
| | FREE FATTY ACID (mmol/L) | | 0.74 | | | >0.7 | 0.6-0.7 | <0.6 | 0.50 |
| | FERRITIN (ng/mL) | | | | 17 | >108 | 61-108 | <61 | 20 |
| | α-HYDROXYBUTYRATE (μg/mL) | | 7.7 | | | >5.7 | 4.5-5.7 | <4.5 | 4.8 |
| | OLEIC ACID (μg/mL) | | 83 | | | >79 | 60-79 | <60 | 54 |
| | LINOLEOYL-GPC (μg/mL) | | | | 24.5 | <10.5 | 10.5-13.0 | >13.0 | 10.9 |
| | IR SCORE | | | | 11.3 | <8.0 | 8.0-10.0 | >10.0 | 11.0 |
| | HOMA-IR | | | | 0.7 | >4.2 | 2.6-4.2 | <2.6 | 1.3 |

METHOD OF TREATING A PATIENT DETERMINED TO BE AT RISK OF DEVELOPING OCCULT PANCREATIC BETA-CELL DYSFUNCTION

PRIORITY CLAIM

This application claims priority under 35 U.S.C. § 119(e) to U.S. Provisional Application No. 61/751,328, filed Jan. 11, 2013, U.S. Provisional Application No. 61/831,337, filed Jun. 5, 2013, and U.S. Provisional Application No. 61/831,405, filed Jun. 5, 2013, all of which are hereby incorporated by reference in their entirety.

BACKGROUND

Currently a number of tests exist that can diagnose patients as diabetic or pre-diabetic, including pre-diabetic conditions, such as occult pancreatic beta cell dysfunction or post-prandial hyperglycemia. Such tests include glucose, insulin, pro-insulin, c-peptide, HbA1c, fructosamine, glycation gap, 1,5-anhydroglucitol (1,5-AG), OGTT, CLIX scoring, HOMA IR scoring, and IRI scores based on combinations of AHB, L-GPC, and Oleic Acid weighted by insulin or BMI. Used alone or in combination some of these tests can detect the presence of Type 2 diabetes, pre-diabetes (metabolic syndrome) and early insulin resistance. Additionally there are tests that may detect some cases of Type 1 Diabetes (T1DM, sometimes referred to as childhood-onset or early-onset) such as anti-GAD antibody and other auto-antibodies to pancreatic islet cells, as Type 1 diabetes usually involves development of auto-antibodies.

The best current predictors of fasting normoglycemic patients who are actually at risk of developing diabetes are OGTTs and CLIX scoring of OGTTs. Both of these techniques involve testing multiple analytes at multiple timepoints, requiring the patient to have a blood sample drawn at baseline (fasting), drink a beverage containing a known quantity of glucose, and subsequently contacting patient blood samples and measuring the levels of various analytes (e.g. glucose, insulin, pro-insulin, c-peptide, creatinine, etc. . . . ) at fasting baseline, and then at various time point intervals after dosing with the glucose load. Most OGTTs and CLIX scoring require a patient to remain in the doctor's office for 2 hours post dose, and most clinicians only test baseline samples and the 2 hour time point, and not the labor-intensive 3-5 additional times blood draws during the 2-hour period necessary for CLIX scoring, due to labor and cost constraints. Additionally, complicated and laborious mathematical calculations need to be performed in order to optimize detection of at-risk individuals with these techniques, and kidney function (approximated by blood creatinine levels/eGFR) needs to be accounted for, causing an additional step. In standard OGTTs, 1-hour time points are rarely obtained and tested for determination of early insulin resistance and/or beta cell dysfunction, even though it is known from the literature that impaired first-phase insulin secretion response to glucose load at the 1 hour time point is a predictor of risk of development of diabetes and resulting cardio-diabetic complications such as atherosclerosis, coronary artery disease, diabetic retinopathy, etc.

There therefore exists a need in the art for a better method for detecting the presence of likelihood of developing occult pancreatic beta cell dysfunction and post-prandial hyperglycemia.

SUMMARY OF INVENTION

This invention relates to a method for detecting the presence of or likelihood of developing occult pancreatic beta cell dysfunction in a patient, comprising: (a) measuring a level of alpha-hydroxybutyrate (AHB) in a single fasting baseline biological sample of the patient; (b) comparing the level of AHB in the single fasting baseline biological sample to a reference AHB level; and (c) determining the presence of or likelihood of developing occult pancreatic beta cell dysfunction in said patient based on the comparison in step (b). An increased AHB level at fasting baseline indicates that a normoglycemic, normo-insulinemic and/or non-dyslipidemic patient has developed or has an increased likelihood of developing occult pancreatic beta cell dysfunction. The level of AHB may be greater than 4.5 µg/mL.

The method may include measuring one or more additional biomarkers in one or more biological samples of the patient. Biomarkers may be selected from glucose, insulin, HDL, HDL-c, triglycerides, LDL, LDL-c, C-peptide, 1, 5-anhydroglucitol, or pro-insulin. Alternatively, the biomarkers may be auto-antibodies present in type-1 diabetes, viral nucleic acids, biomarkers to autoimmune diseases, viral DNAs, or viral RNAs and antibodies to viral capsid proteins for members of the Enterovirus family. Alternatively, the biomarkers may be glucose, insulin, anti-islet cell cytoplasmic (anti-ICA) auto-antibodies, glutamic acid decarboxylase (anti-GAD) auto-antibodies, 1, 5-anhydroglucitol, hemoglobin (Hb) A1c, fructosamine, mannose, D-mannose, mannose-binding lectin (MBL) amount, mannose binding lectin (MBL) activity, 1,5-anhydroglucitol (1,5 AG), glycation gap (glycosylation gap), serum amylase, c-peptide, intact pro-insulin, leptin, adiponectin, leptin/adiponectin ratio, ferritin, free fatty acids, lipoprotein-associated phospholipase A2 (Lp-PLA2), fibrinogen, myeloperoxidase, cystatin C, homocysteine, F2-isoprostanes, a-hydroxybutyrate (AHB), linoleoyl glycerophosphocholine (L-GPC), oleic acid (OA), analytes associated with IR score, analytes associated with HOMA (Homeostasis Model Assessment) IR score, analytes associated with CLIX score, gamma-glutamic transferase (GGT), uric acid, vitamin B12, homocysteine, 25-hydroxyvitamin D, TSH, estimated glomerular filtration rate (eGFR), or serum creatinine. Alternatively, the biomarkers may be biomarkers associated with body mass index (BMI), free fatty acids, low density lipoprotein particle number (LDL-P), LDL-cholesterol (LDL-C), triglyceride; high density lipoprotein particle number (HDL-P), high density lipoprotein-cholesterol (HDL-C), high sensitivity C-reactive protein (hs-CRP), remnant-like lipoproteins (RLPs), RLP- (cholesterol measures), apolipoprotein A-1, HDL2, ApoB:ApoA-1 ratio, Lp(a) mass, Lp(a) cholesterol, large VLDL-P, small LDL-P, large HDL-P, VLDL-size, LDL size, HDL size, LP-IR score, apolipoprotein A-1 (ApoA-1), apolipoprotein B (ApoB), apolipoprotein C (ApoC), apolipoprotein E (ApoE), ApoE sub-species, or variations, fragments, PTMs and isoforms thereof. Alternatively, biomarkers may be campesterol, sitosterol ((3-sitosterol), cholestanol, desmosterol, lathosterol, or squalene. Alternatively, the biomarkers may be biomarkers for coagulation or dyslipidemia.

A determination of increased likelihood of an impaired first phase insulin secretion response can be based on the determination in 1 (c).

The presence of or increased likelihood of developing occult pancreatic beta cell dysfunction also indicates that said patient is at risk of a diabetic condition, such as cardiodiabetes, gestational diabetes, latent autoimmune diabetes of adults (LADA), mixed phenotype diabetic conditions, or atypical forms of type 1 diabetes, such as insulin autoimmune syndrome (IAS).

The presence of or increased likelihood of developing pancreatic beta cell dysfunction can also be used to predict an increased likelihood of a requirement for exogenous insulin supplementation. The method can also be used to show that the patient is at risk for a cardiodiabetic disease associated with post-prandial hyperglycemia. Types of cardiodiabetic disease include retinopathy, neuropathy, nephropathy, atherosclerosis, stroke, myocardial infarction, gestational diabetes, pre-term labor, and the birth of high birth-weight infants.

The patient may or may not show signs associated with any apparent beta cell dysfunction, as detected by conventional diagnostic techniques.

Determination step (c) may be performed without having the patient provide multiple biological samples separated by a period of time.

A health risk value may be assigned for the patient based on the determination in step (c), The health risk value may be low risk, moderate risk and high risk of occult pancreatic beta cell dysfunction.

In one embodiment, an AHB level of less than 4.5 µg/mL indicates a low risk of occult pancreatic beta cell dysfunction; an AHB level of about 4.5 µg/mL to about 5.7 µg/mL indicates an intermediate to a high risk of occult pancreatic beta cell dysfunction; and an AHB level of more than 5.7 µg/mL indicates a high risk of occult pancreatic beta cell dysfunction.

The method may include measuring the anti-ICA or anti-GAD auto-antibodies biomarkers in the biological sample, wherein a positive reaction to one of the biomarkers indicates an increased risk of occult pancreatic beta cell dysfunction.

A therapy guidance may be effectuated based on the determination in step (c). Suitable therapy guidance includes one or more of the following: performing a confirmatory OGTT and/or additional diagnostic testing, prescribing a drug therapy, increasing monitoring frequency of patient condition, and recommending appropriate risk-reduction therapy such as making or maintaining diet and lifestyle choices based on the determination in step (c). The therapy guidance may involves administration of antioxidants, administration of anti-coagulants, administration of anti-dyslipidemic drugs, avoidance of drugs or agents known to damage pancreatic cells; discontinued administration of current drug therapy, administration of agents specific for post-prandial hyperglycemia (e.g. cycloset), administration of drugs that enhance, and/or augment, and/or spare pancreatic beta cell function, administration of an anti-viral agent, an immunosuppressant or insulin or an insulin analog or combinations thereof. The therapy guidance may also include one or more of the following: increased frequency of physician's follow-up, referral for oral glucose tolerance test (OGTT) and/or CLIX test, repetition of tests for monitoring disease progression, patient referral for comprehensive testing for type I diabetes; testing for auto-antibodies to pancreatic cell antigens, other biomarkers for autoimmune diseases, viral DNA/RNA and/or antibodies to viral capsid proteins for Enterovirus family members or combinations thereof. A lifestyle choices involve changes in diet and nutrition, changes in exercise, smoking elimination or a combination thereof.

The biological sample may be a blood component, saliva or urine.

Another embodiment of the invention relates to a method for detecting the presence of or likelihood of a patient of developing occult pancreatic beta cell dysfunction, comprising: (a) measuring a level of alpha-hydroxybutyrate (AHB) in a biological sample of the patient; (b) comparing the level of AHB in the baseline biological sample to a reference AHB level; and (c) determining the presence of or likelihood of the patient to develop occult pancreatic beta cell dysfunction based on the comparison in step (b). The determination in step (c) is performed without having the patient provide multiple biological samples separated by a period of time. An elevated AHB baseline level indicates that a normoglycemic, normo-insulinemic and/or nondyslipidemic patient has developed or has an increased likelihood of developing occult pancreatic beta cell dysfunction.

Another embodiment of the invention relates to a method for monitoring the progression or remission or a patient's response to treatment of a diabetic condition due to occult pancreatic beta cell dysfunction in a patient, comprising: (a) measuring a first level of alpha-hydroxybutyrate (AHB) in a biological sample of the patient; (b) measuring a second level of alpha-hydroxybutyrate (AHB) in the biological sample of the patient after a period of time; (c) comparing the first level and the second level of AHB in the biological sample based on the measurements in steps (a) and (b) to determine whether the level of AHB has changed; and (d) monitoring the patient's progression or remission or the patient's response to treatment of the diabetic condition based on the comparison in step (c). An increased AHB level or an unchanged AHB level indicates that the diabetic condition is still in progression and/or a normoglycemic, normo-insulinemic and/or non-dyslipidemic patient is not responding to the treatment. A decreased AHB level indicates that the diabetic condition is in remission and/or a normoglycemic, normo-insulinemic and/or non-dyslipidemic patient is responding to the treatment. The measurement in step (b) may be taken at least one day after the measurement in step (a).

When relating to monitoring a patient's response to a treatment, the method may further comprise the step of adding a treatment, after the measurement in step (a), to treat the diabetic condition; the method may also further comprises the step of changing and/or discontinuing a treatment, after the measurement in step (a), to treat the diabetic condition.

Another embodiment of this invention relates to a method for detecting the presence of or likelihood of developing clinically significant post-prandial hyperglycemia in a patient, comprising: (a) measuring a level of alpha-hydroxybutyrate (AHB) in a single fasting baseline biological sample of the patient; (b) comparing the level of AHB in the single fasting baseline biological sample to a reference AHB level; and (c) determining the presence of or likelihood of developing clinically significant post-prandial hyperglycemia based on the comparison in step (b). An increased AHB level at fasting baseline and an elevated glucose level of at least about 155 mg/dL at 30 minutes and/or 1 hour indicates that a normoglycemic, normo-insulinemic and/or non-dyslipidemic patient has developed or has an increased likelihood of developing clinically significant post-prandial hyperglycemia. The level of AHB may be greater than 4.5 µg/mL.

The method may include measuring one or more additional biomarkers in one or more biological samples of the patient. Biomarkers may be selected from glucose, insulin, HDL, HDL-c, triglycerides, LDL, LDL-c, C-peptide, 1, 5-anhydroglucitol, or pro-insulin. Alternatively, the biomarkers may be auto-antibodies present in type-1 diabetes, viral nucleic acids, biomarkers to autoimmune diseases, viral DNAs, or viral RNAs and antibodies to viral capsid proteins for members of the Enterovirus family. Alternatively, the biomarkers may be glucose, insulin, anti-islet cell cytoplasmic (anti-ICA) auto-antibodies, glutamic acid decarboxylase (anti-GAD) auto-antibodies, 1, 5-anhydroglucitol, hemoglobin (Hb) A1c, fructosamine, mannose, D-mannose, mannose-binding lectin (MBL) amount, mannose binding lectin (MBL) activity, 1,5-anhydroglucitol (1,5 AG), glycation gap (glycosylation gap), serum amylase, c-peptide, intact pro-insulin, leptin, adiponectin, leptin/adiponectin ratio, ferritin, free fatty acids, lipoprotein-associated phospholipase A2 (Lp-PLA2), fibrinogen, myeloperoxidase, cystatin C, homocysteine, F2-isoprostanes, a-hydroxybutyrate (AHB), linoleoyl glycerophosphocholine (L-GPC), oleic acid (OA), analytes associated with IR score, analytes associated with HOMA (Homeostasis Model Assessment) IR score, analytes associated with CLIX score, gamma-glutamic transferase (GGT), uric acid, vitamin B12, homocysteine, 25-hydroxyvitamin D, TSH, estimated glomerular filtration rate (eGFR), or serum creatinine. Alternatively, the biomarkers may be biomarkers associated with body mass index (BMI), free fatty acids, low density lipoprotein particle number (LDL-P), LDL-cholesterol (LDL-C), triglyceride; high density lipoprotein particle number (HDL-P), high density lipoprotein-cholesterol (HDL-C), high sensitivity C-reactive protein (hs-CRP), remnant-like lipoproteins (RLPs), RLP- (cholesterol measures), apolipoprotein A-1, HDL2, ApoB:ApoA-1 ratio, Lp(a) mass, Lp(a) cholesterol, large VLDL-P, small LDL-P, large HDL-P, VLDL-size, LDL size, HDL size, LP-IR score, apolipoprotein A-1 (ApoA-1), apolipoprotein B (ApoB), apolipoprotein C (ApoC), apolipoprotein E (ApoE), ApoE sub-species, or variations, fragments, PTMs and isoforms thereof. Alternatively, biomarkers may be campesterol, sitosterol ((3-sitosterol), cholestanol, desmosterol, lathosterol, or squalene. Alternatively, the biomarkers may be biomarkers for coagulation or dyslipidemia.

The method may further comprise administering an oral glucose tolerance test (OGTT). If the patient exhibits a glucose level of at least about 155 mg/dL and/or a decreased first phase insulin response within one hour of taking OGTT and/or after food consumption, this is an additional indication of clinically significant post-prandial hyperglycemia, or that the patient has developed or has an increased likelihood of developing clinically significant post-prandial hyperglycemia.

The presence of or increased likelihood of developing clinically significant post-prandial hyperglycemia also indicates that said patient is at risk of a diabetic condition, such as cardiodiabetes, gestational diabetes, latent autoimmune diabetes of adults (LADA), mixed phenotype diabetic conditions, or atypical forms of type 1 diabetes, such as insulin autoimmune syndrome (IAS).

The presence of or increased likelihood of developing clinically significant post-prandial hyperglycemia can also be used to predict an increased likelihood of a requirement for exogenous insulin supplementation. The method can also be used to show that the patient is at risk for a cardiodiabetic disease associated with post-prandial hyperglycemia. Types of cardiodiabetic disease include retinopathy, neuropathy, nephropathy, atherosclerosis, stroke, myocardial infarction, gestational diabetes, pre-term labor, and the birth of high birth-weight infants.

The method may further comprise measuring the biological sample with the biomarker 1,5-anhydroglucitol. An elevated level of AHB and a normal level of 1, 5-anhydroglucitol at baseline can be used as a guide to determine whether the post-prandial hyperglycemia does not exceed the glucose renal threshold, for instance a glucose renal threshold of at least about 180 mg/dL.

The patient may show no clinically significant post-prandial hyperglycemia, as detected by conventional diagnostic techniques.

Determination step (c) may be performed without having the patient provide multiple biological samples separated by a period of time.

A health risk value may be assigned for the patient based on the determination in step (c). The health risk value may be low risk, moderate risk and high risk of occult pancreatic beta cell dysfunction.

In one embodiment, an AHB level of less than 4.5 µg/mL indicates a low risk of clinically significant post-prandial hyperglycemia; an AHB level of about 4.5 µg/mL to about 6.0 µg/mL indicates an intermediate to a high risk of clinically significant post-prandial hyperglycemia; and an AHB level of more than 6.0 µg/mL indicates a high risk of clinically significant post-prandial hyperglycemia.

The method may include measuring the anti-ICA or anti-GAD auto-antibodies biomarkers in the biological sample, wherein a positive reaction to one of the biomarkers indicates an increased risk of clinically significant post-prandial hyperglycemia.

A therapy guidance may be effectuated based on the determination in step (c). Suitable therapy guidance includes one or more of the following: performing a confirmatory OGTT and/or additional diagnostic testing, prescribing a drug therapy, increasing monitoring frequency of patient condition, and recommending appropriate risk-reduction therapy such as making or maintaining diet and lifestyle choices based on the determination in step (c). The therapy guidance may involves administration of antioxidants, administration of anti-coagulants, administration of anti-dyslipidemic drugs, avoidance of drugs or agents known to damage pancreatic cells; discontinued administration of current drug therapy, administration of agents specific for post-prandial hyperglycemia (e.g. cycloset), administration of drugs that enhance, and/or augment, and/or spare pancreatic beta cell function, administration of an anti-viral agent, an immunosuppressant or insulin or an insulin analog or combinations thereof. The therapy guidance may also include one or more of the following: increased frequency of physician's follow-up, referral for oral glucose tolerance test (OGTT) and/or CLIX test, repetition of tests for monitoring disease progression, patient referral for comprehensive testing for type I diabetes; testing for auto-antibodies to pancreatic cell antigens, other biomarkers for autoimmune diseases, viral DNA/RNA and/or antibodies to viral capsid proteins for Enterovirus family members or combinations thereof. A lifestyle choices involve changes in diet and nutrition, changes in exercise, smoking elimination or a combination thereof.

The biological sample may be a blood component, saliva, or urine.

Additional aspects, advantages and features of the invention are set forth in this specification, and in part will become apparent to those skilled in the art on examination of the following, or may learned by practice of the invention. The inventions disclosed in this application are not limited to any particular set of or combination of aspects, advantages and features. It is contemplated that various combinations of the stated aspects, advantages and features make up the inventions disclosed in this application.

BRIEF DESCRIPTION OF THE DRAWINGS

FIG. 15 shows a distribution of beta cell CLIX score with two identified outlier observations.

FIGS. 16A-C show lipid profiles of Patient X at six time points. FIG. 16A shows that no lipid test was conducted on Feb. 28, 2012 and Apr. 3, 2012. FIG. 16B shows the results of the lipid tests conducted on May 2, 2012 and Jul. 10, 2012. FIG. 16C shows the results of the lipid tests conducted on Jan. 8, 2013 and Feb. 27, 2013.

FIGS. 17A-C show the test results for biomarkers of Glycemic Control, Beta Cell Function and Insulin Resistance of Patient X at six time points. FIG. 17A shows that biomarker test results from Feb. 28, 2012 and Apr. 3, 2012. FIG. 17B shows biomarker test results from May 2, 2012 and Jul. 10, 2012. FIG. 17C shows biomarker test results from Jan. 8, 2013 and Feb. 27, 2013.

DETAILED DESCRIPTION

Figure 1:
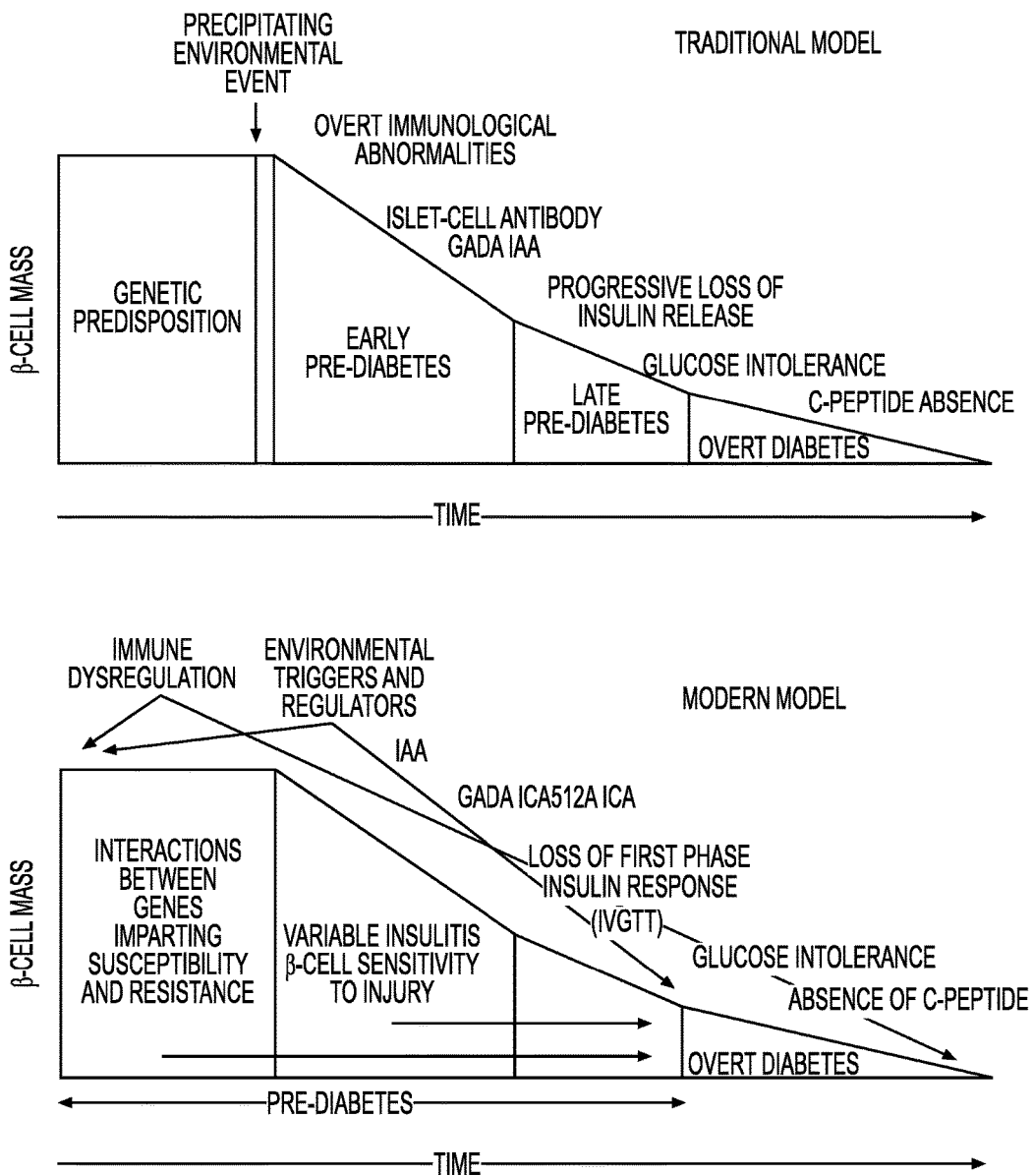
FIG. 1 shows the traditional and modern models for onset of type 1 diabetic mellitus (T1DM), adapted from Atkinson and Eisenbarth, Type 1 diabetes: new perspective on disease pathogenesis and treatment, The Lancet, 358(9277):221-229 (2009).

This invention provides a diagnostic tool that enables the detection and identification of a subset of apparently normal (normoglycemic and non-dyslipidemic) patients, from a single fasting baseline sample, who have occult pancreatic beta cell dysfunction resulting in impaired first-phase insulin response. The clinical utility of the invention arises from identification of asymptomatic patients at increased risk of developing full-blown diabetes from pancreatic insufficiency early in the progression of the disease. This test identifies forms of diabetes with features of both Type 1 and Type 2 and slow progression to insulin insufficiency such as (LADA), "skinny diabetes," which is more frequently observed in Asian populations, and atypical forms of Type 1 diabetes such as Insulin Autoimmune Syndrome (IAS) in apparently normal, healthy patients. Detecting patients who would be mis-diagnosed as "normal" (no apparent beta cell dysfunction) by conventional diagnostic testing procedures will result in earlier identification of at-risk patients so that they can be targeted for optimal therapeutic intervention to delay or prevent disease progression, and improve clinical outcomes.

Existing Test Cut-Offs and Definitions of Disease

The control of blood glucose levels is critical. Insulin is the hormone that brings blood glucose into cells. Without sufficient insulin to bring glucose into the cells, blood glucose becomes elevated, and the cells "starve" for glucose and the body must use alternative pathways to produce energy for vital organs, like generating ketone bodies and free fatty acids (FFA's) to fuel the brain and heart, respectively. The pancreatic beta cells normally secrete insulin in response to a meal or a "glucose load" during an oral glucose tolerance test (OGTT), thus bringing down the level of blood glucose by bringing it into the cells of the body. This process of glucose homeostasis can be dysregulated in a number of ways, resulting in poor control of blood glucose levels. When glucose balance is dysregulated such that blood glucose varies to higher than normal for short or long periods of time, this means that the patient has developed or is developing diabetes.

Type 1 Diabetes (T1DM). There are multiple types of diabetes; it is not a single disease. Decades ago, the predominant type of diabetes was known as "early onset" and it was an acute illness usually occurring in childhood or adolescence in which the patient would suddenly go from healthy to very sick, with high blood sugar due to rapid and catastrophic failure of the pancreas to produce enough insulin. The patient would require injections of insulin in order to maintain normal levels of blood sugar and survive. Today we call this Type 1 Diabetes Mellitus (T1DM) and recognize that the cause is usually viral infection and/or autoimmunity, and that this form occurs in adults as well as children. Full-blown T1DM requires that patients be treated with exogenous insulin, because patients do not make enough insulin by themselves to survive. However, there are milder forms of T1DM that progress more slowly to insulin-dependence, or in which a patient may need insulin for a short period of time, and then go off of the insulin and maintain their normal blood glucose regulation.

Type 2 Diabetes (T2DM) is completely different physiologically to T1DM. T2DM is characterized by abnormally high blood glucose and abnormally high insulin levels. Also, T2DM does not have an acute onset of symptoms like T1DM. In contrast, it develops gradually over time, usually years, and therefore used to be called "adult onset" diabetes. T2DM is related to diet and lifestyle factors such as eating a high-sugar, high-carbohydrate diet, lack of exercise, and development of obesity, in particular abdominal obesity. Because of the sedentary lifestyle and poor diet in the Western world, there is an epidemic of T2DM in the US and Europe that parallels the rise in the number of obese and morbidly obese adults. Because more children are also becoming obese, we now see more cases of T2DM developing in childhood. The consequences for development of T2DM is a radical increase in the risk of cardiovascular disease, termed cardiodiabetes, such as increased risk of heart attacks, strokes, high blood pressure, atherosclerosis, coronary artery disease, etc. . . . .

Insulin Resistance. The development of T2DM is preceded by years of abnormal metabolism during which lifestyle and diet intervention, including weight loss, can completely prevent and reverse the development of the disease in most people. The earliest stage of T2DM is called "insulin resistance" and most patients exhibit signs of the "metabolic syndrome." The initial clinical presentation associated with insulin resistance is hyperinsulinemia, impaired glucose tolerance, dyslipidemia [hypertriglyceridemia and decreased high-density lipoprotein (HDL) cholesterol] and hypertension. We also know that chronic inflammation can help drive the development of insulin resistance. Insulin resistance is a change in physiologic regulation such that a fixed dose of insulin causes less of an effect on glucose metabolism than occurs in normal individuals (blood glucose does not drop as much or as fast as it should in response to increases in insulin). The normal compensatory response to insulin resistance is an even higher increase in insulin secretion that results in hyperinsulinemia. If the hyperinsulinemia is sufficient to overcome the insulin resistance, glucose regulation remains normal; if not, type 2 diabetes ensues.

"Metabolic syndrome" is associated with insulin resistance; this is a cluster of metabolic abnormalities involving body fat distribution, lipid metabolism, thrombosis, blood pressure regulation, and endothelial cell function. This cluster of abnormalities is referred to as the insulin resistance syndrome or the metabolic syndrome. Eventually, blood glucose remains elevated even in the fasting state as the insulin resistant patient progresses towards T2DM. The pancreatic beta cells must work very hard to pump out this much insulin, and over time, the pancreatic islets (and the beta cells they contain) are damaged due to what can be thought of as exhaustion. The beta cells begin to secrete more immature insulin (pro-insulin) in an attempt to keep up with the demand, and therefore in the blood of people who are insulin resistant and well on their way to developing T2DM we see biomarkers of pancreatic beta cell dysfunction such as higher levels of insulin, pro-insulin and c-peptide. An excellent review of Insulin Resistance and all the various tests and indices used to diagnose insulin resistance and gauge its severity is "Surrogate markers of insulin resistance: A review" by Bhawna Singh and Alpana Saxena, 2010.

"Pre-diabetes". This term is essentially synonymous with insulin resistance and metabolic syndrome of Type 2 Diabetes, but has specific lab values associated with it. Doctors screen patients for diabetes if they have known risk factors, a family history of diabetes, high blood pressure, BMI greater than 25, or if they have abnormal cholesterol levels (defined as HDL-C below 35 mg/dL (0.9 mmol/L) or triglyceride level above 250 mg/dL (2.83 mmol/L). Tests used to diagnose pre-diabetes include the Glycated hemoglobin (HbA1C) test (6.0 to 6.5 percent is the pre-diabetes range), a fasting blood glucose level from 100 to 125 mg/dL (5.6 to 6.9 mmol/L), or a blood glucose value of 140 to 199 mg/dL (7.8 to 11.0 mmol/L) at the 2-hour time point of an OGTT. It is this elevation of 2-hour blood glucose value that defines a patient as having "impaired glucose tolerance" (IGT. If the patient has pre-diabetes, doctors will usually test fasting blood glucose, HbA1C, total cholesterol, HDL cholesterol, low-density lipoprotein (LDL) cholesterol and triglycerides at least once a year. Note that the above lab values do not describe the patient population in which HDL is claiming utility of elevated baseline AHB for pancreatic beta cell dysfunction.

If full-blown T2DM develops and is left undiagnosed and untreated, patients must be treated with insulin-sensitizing drugs which may help make their cells more responsive to insulin, and the pancreas does not have to work as hard. Blood glucose balance can be maintained with insulin sensitizing drugs, or maintained and/or reversed by the addition of diet and lifestyle modifications and weight loss. Unlike full-blown T1DM, T2DM may be reversible in many patients. However, if T2DM progresses far enough, the pancreatic beta cells become unable to secrete enough insulin on their own due to exhaustion and the patient may progress to the last stage of T2DM wherein they cannot make enough insulin, and therefore will become insulin-dependent and must inject exogenous insulin to survive because their pancreatic beta cells no longer function. This is the worst stage of T2DM and can be fatal because while a patient can be administered exogenous insulin, their body may still be resistant to its effects. These patients are at dramatically increased risk for cardio-diabetic morbidity and mortality.

Disorders of Glucose Metabolism

Disorders of glucose metabolism on the sliding scale of T2DM are defined per the following laboratory test values:

Insulin resistance (IR): a state in which higher concentrations of insulin are required to exert normal effects; blood glucose levels may be normal but fasting insulin levels may be high because of compensatory insulin secretion by the pancreas. Optimal fasting insulin level is defined by HDL as 3-9 µU/mL, intermediate is defined as >9 and <12, and high is defined as >12.

"Pre-diabetes"=Impaired glucose tolerance (IGT): glucose 140-199 mg/dL 2 hours after a 75 g oral glucose load Impaired fasting glucose: glucose 100-125 mg/dL after an 8-hour fast Diabetes mellitus (DM): any of the following four criteria may be used (results must be confirmed by retesting on a subsequent occasion): fasting glucose >126 mg/dL; glycosylated hemoglobin (HbA1c) level >6.5%; 2-hour glucose level >200 mg/dL during glucose tolerance testing; or random glucose values >200 mg/dL in the presence of symptoms of hyperglycemia.

It will be appreciated by those skilled in the art of diabetes diagnostics and treatment that the patient population in which this invention has clinical utility do not fit the above clinical definitions for insulin resistance, pre-diabetes, metabolic syndrome, impaired fasting glucose, T2DM, or T1DM (insulin-dependent). This test does not detect insulin resistance or place a patient on a scale between normal glucose tolerance (NGT) and diabetes, because the patient population in which the test predicts abnormal first-phase insulin response are by definition NGT with normal glucose and insulin levels at baseline and the 2 hour time point, and do not meet the definition of insulin resistance based on their lipid values on the LP-IR scale. Thus, while for the purpose of illustrating the utility of the invention we split the patients into groups by glucose tolerance and degree of insulin resistance for the purpose of analyzing data in the different groups, this is for illustrative purposes to show the utility of the test in the NGT, non-insulin resistant "normal" group. The test does not have clinical utility as an early predictor of risk once the patient has met the criteria for Impaired Glucose Tolerance (IGT) or Diabetes.

Relationship of First and Second-Phase Insulin Response to Beta Cell Function in Health and Diabetes When patients are challenged with a glucose load in an OGTT, and when they eat meals, blood glucose rises, and the pancreatic beta cells detect the post-prandial rise in blood glucose. The beta cells normally react by releasing a rapid burst of insulin termed the "first phase" response from 2-15 minutes after a glucose load or mixed meal. The first phase response is followed by a second phase response, which is a slower and more sustained release of insulin sufficient to return the blood glucose to normal fasting levels, usually by 120 minutes (2 hours). Insulin should also return to normal levels by the 2 hour time point in a healthy individual with no pancreatic beta cell dysfunction and normal glucose tolerance.

In non-diabetic individuals, half of the total daily insulin is secreted during basal periods; this suppresses lipolysis, proteolysis, and glycogenolysis. The other half of insulin secretion occurs postprandially. In response to a meal, the first phase insulin secretion response should be a rapid and sizable release of preformed insulin from storage granules within the beta cell in non-diabetic individuals. The first phase of insulin secretion promotes peripheral utilization of the prandial glucose load, and also suppresses hepatic glucose production, thus limiting postprandial glucose elevation.

Comparison of inter-individual first-phase insulin response to an intravenous glucose bolus serves as a standardized way to measure beta cell function among different subjects. A blunting of or loss of first phase response signals beta-cell declines early in the development of type 1 or later in the development of type 2 diabetes, even while responses to amino acid and other stimuli may be preserved.

In Type 1 and Type 2 diabetics, first phase and second phase insulin responses are altered in different ways during disease onset and progression. In T2DM (as illustrated in the FIG. 1, published in The Lancet, 2009)), note that years before diagnosis of T2DM the overall insulin secretion is greater than normal (mostly due to increased second phase response). During this period, the cells of the patient become more and more resistant to the effects of insulin, causing blood glucose to rise and despite the hyperinsulinemic state. In the classical view of onset of T2DM, the beta cells do begin to fail later in the disease and is accompanied by insulin resistance and (usually) components of the metabolic syndrome.

T1DM has a very different presentation to T2DM. In T1DM, the disease progression does not have an early hyperinsulinemic phase of increased beta cell function prior to the decline in function, and insulin resistance and metabolic syndrome generally do not contribute to the pathology. In T1DM, the beta cell function begins to deteriorate, usually slowly over time prior to overt symptoms of hypoinsulinemia, the resulting hyper-glycemia, and disease diagnosis. The figure below compares first and second phase insulin response in a normal patient vs. T1DM and T2DM patients late in the course of the disease. Note that the T2DM patients have a blunted first-phase response but enhanced second phase, whereas the full-blown T1DM patient has no first or second phase insulin response and would therefore be dependent on exogenous insulin for survival.

The complete ablation of beta cell function and insulin response in T1DM is, however, preceded by measurable incremental declines, especially in the case of adult-onset T1DM, which tends to be more gradual and less acute than childhood onset T1DM. The figure below illustrates the general time-course of development of T1DM and correlates the loss of beta cell mass (loss of cells, loss of function) to various events and triggers in the time period leading up to prior to detectable blunted insulin secretion and diagnosis of T1DM. Currently an asymptomatic patient with normal baseline glucose and normal baseline insulin levels would be considered normal and would not be screened for T1DM; in the event that an OGTT test was performed on such a patient and the beta cells were not sufficiently compromised to give abnormal 2-hour time point values, the early onset of blunted first phase response would be missed. However, testing at earlier time points in an OGTT such as prior to 1 hour would reveal blunted first phase response which is the earliest indicator of deterioration of beta cell on the continuum of T1DM development. However, in a patient with no discernible risk factors for development of diabetes, and/or no abnormal baseline values in fasting blood glucose or insulin, a physician would not order and OGTT and thus the subclinical deterioration in beta cell function would not be detected, resulting in a missed opportunity to identify an at-risk patient and intervene clinically to prevent disease progression.

Until recently it was thought that the destruction of the beta cells was wholly attributable to an auto-immune attack, and that diagnosis of disease onset was measurable by detection of anti-pancreatic island auto-antibodies (IAA) such as anti-GAD and others, and that onset of disease and destruction of beta cell function was triggered by the auto-immune reaction. Thus it was thought in the past that there was no impaired first-phase response until after development of auto-antibodies.

Now it is thought that the deterioration in beta cell function and impaired first-phase response begins prior to appearance of auto-immunity and that the development of auto-immunity is an adaptive, protective response to ongoing beta cell damage, rather than a precipitating event in and of itself. It is now recognized that there are metabolic abnormalities and environmental insults that, in combination with genetic risk factors predisposing a patient to susceptibility to development of T1DM, combine to initiate development of the disease.

FIG. 1 shows the traditional model as well as the modern model for onset of T1DM and illustrates that there is a clear window of beta cell decline which, if detected early, could provide an opportunity for therapeutic intervention to delay or prevent further loss of beta cell function.

Figure 2:
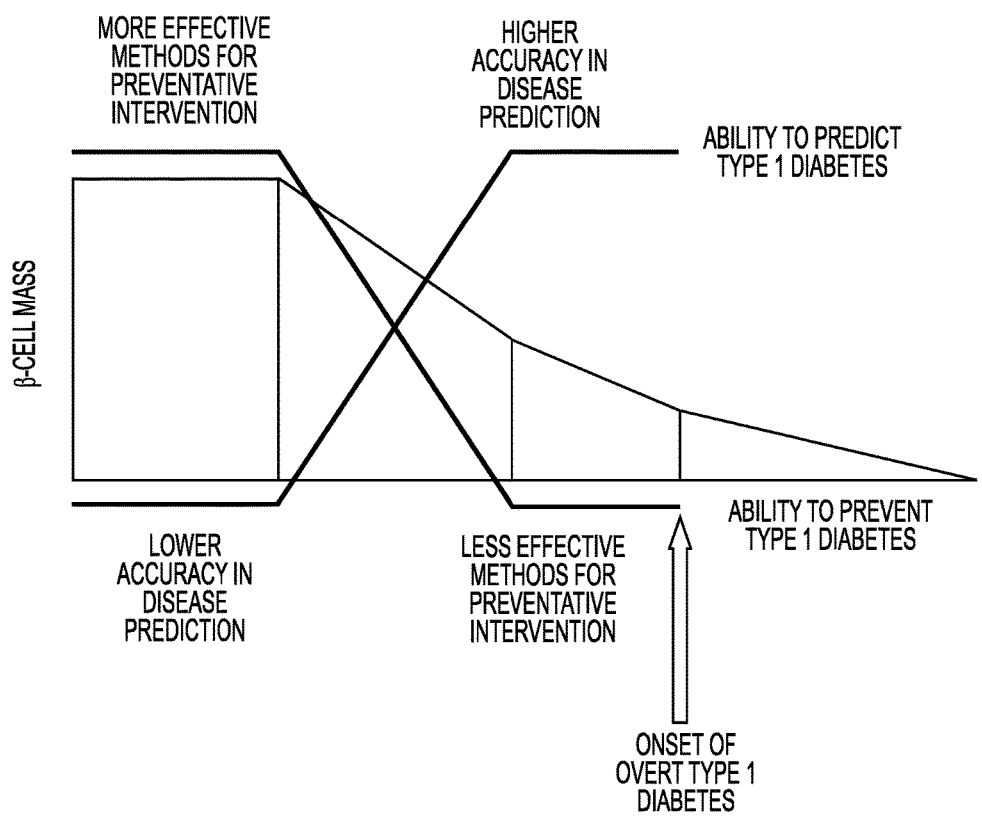
FIG. 2 illustrates a concept showing methods that accurately predict T1DM development early in the course of the disease may be clinically useful in the prevention of full-blown diabetes, adapted from Atkinson and Eisenbarth, Type 1 diabetes: new perspective on disease pathogenesis and treatment, The Lancet, 358(9277):221-229 (2009).

FIG. 2 (also published in The Lancet, 2009) illustrates the concept that tests which are able to accurately predict T1DM development early in the course of the disease, such as tests for early beta cell dysfunction, would be clinically useful in preventing full-blown diabetes. The early detection of subclinical beta cell dysfunction, including impaired first phase insulin secretory response resulting in post-prandial hyperglycemia in the onset of any form of diabetes, is the area of clinical utility for the test described herein.

Figure 3:
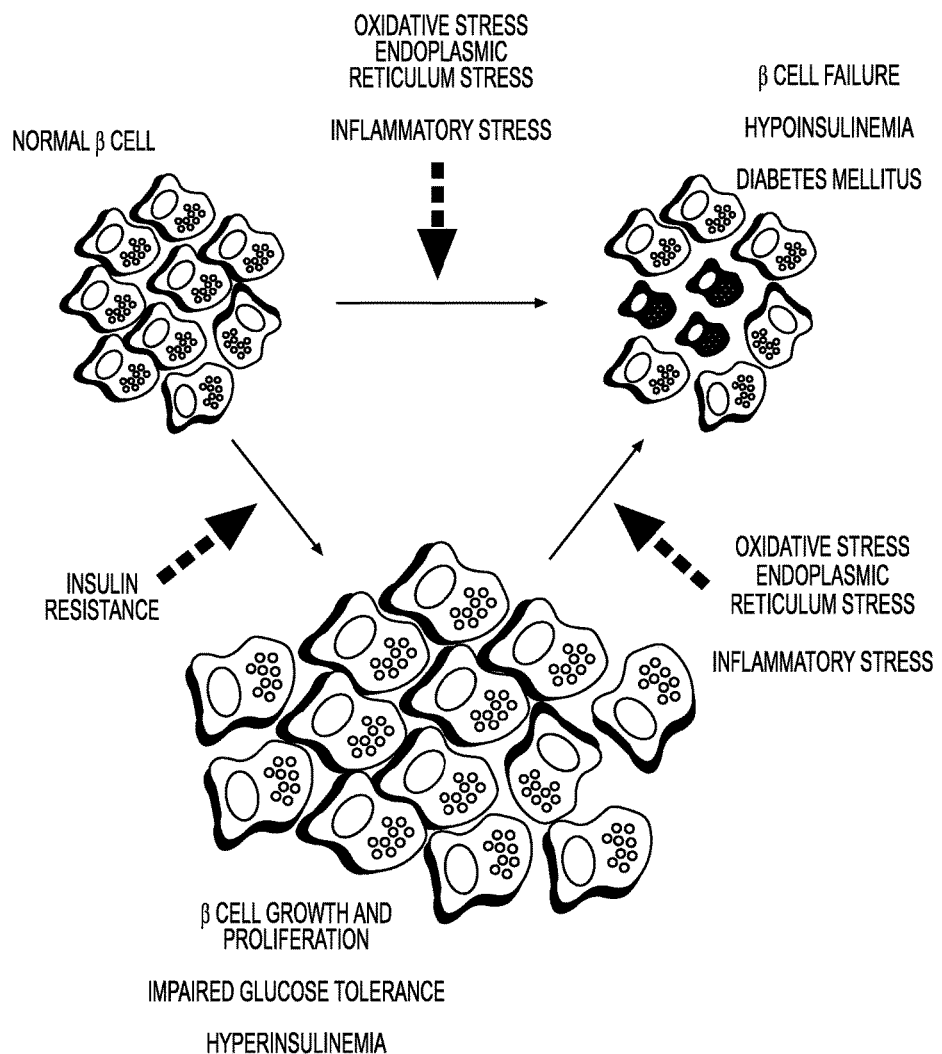
FIG. 3 shows the pathways that lead normal beta cells to become dysfunctional in T1DM versus Type 2 diabetic mellitus (T2DM).

FIG. 3 illustrates how beta cells become dysfunctional in T1DM vs. T2DM. In T1DM, oxidative stress and inflammation damage the beta cells; some individuals seem to be more susceptible to these stressors whereas others are more resistant and therefore less likely to develop T1DM. The damage and recovery or progression is a multi-factorial process that is partially due to genetic risk factors, lifestyle, diet/nutrition, inflammatory events such as infections or autoimmune conditions, metabolic alterations, etc. Ultimately the beta cells cannot adequately recover and repair and begin to secrete less insulin and also die by apoptosis, resulting in fewer functional cells and hypo-insulinemia. In T2DM by contrast there is an intermediate step before beta cell dysfunction and failure wherein the beta cells may proliferate and hypertrophy as the result of hyperglycemia and insulin resistance; this is the early phase in which the patient is hyperinsulinemic to compensate for the hyperglycemia. The demand for insulin production as well as the metabolic changes occurring during progression of insulin resistance to T2DM generates oxidative stress and inflammatory responses, and these then drive the progression of beta cell failure just as in T1DM, but later in the disease state.

Alpha Hydroxybutyrate (AHB)

Current theories about AHB elevations in the context of diabetes are that this metabolite is related to glucose disposal rate resulting from insulin resistance (metabolic syndrome), and that higher levels of AHB particularly with other metabolites such as L-GPC and Oleic Acid are useful for placing patients on a spectrum of insulin resistance (glucose tolerance) in the development of Type 2 diabetes. However, our results clearly show that AHB may not be related to insulin resistance and glucose disposal rate but rather to impaired first phase insulin secretion response that results in clinically significant post-prandial hyperglycemia in apparently NGT individuals.

AHB is also a ketone though it is not glucogenic, and therefore not directly related to metabolism of glucose or alternative substrates. The 2 main ketone bodies are 3-hydroxybutyrate (3HB) and acetoacetate (AcAc). Therefore AHB is not produced like other ketone bodies in the context of altered glucose metabolism.

It is believed that AHB is produced in the liver byproduct during the formation of α-ketobutyrate (a product of either threonine catabolism or methionine metabolism via cystathione) under conditions of excess glutathione demand resulting from high oxidative stress, or conditions that promote high dihydronicotinamide adenine dinucleotidel nicotinamide adenine dinucleotide (NADH/NAD+) levels, such as increased fatty acid oxidation. Glutathione (GSH) is one of the most important molecules for fighting oxidative stress in the human body. Oxidative stress may be caused by inflammation, infection, and environmental factors, and the imbalance between the generation of free radicals and a biological system's ability to readily neutralize the free radicals or to repair the resulting damage results cellular damage and disease. Oxidative stress causes disturbances in the normal redox state of cells resulting in production of toxic peroxides and free radicals that damage proteins, lipids, and DNA by oxidation. It is known that oxidative stress can cause apoptosis and necrosis in cells, including beta cells, which are very sensitive to oxidative damage.

Oxidative stress is involved in all aspects of damage to the body, from pancreatic beta cell damage to atherosclerosis, inflammation, and neuropathy. Autoimmunity and the chronic inflammation it causes also result in significant oxidative stress. Under conditions of metabolic stress, the liver tries to synthesize as much glutathione as possible from precursors L-glutamate and L-Cysteine. L-cysteine becomes rate-limiting for production of GSH under metabolic stress conditions, so more cysteine is made by diverting homocysteine away from methionine synthesis and into a trans-sulfuration pathway to form cystathione. When cystathione is cleaved to cysteine to make glutathione, AHB is released as a by-product and can be detected in blood and urine.

Therefore, the higher the oxidative and metabolic stress (such as from inflammation), the more AHB is released. Therefore it is believed that the appearance of elevated levels of AHB does not signal insulin resistance or the existence of Type 2 diabetes as taught in the current literature, but rather signals the oxidative stress leading to beta cell damage and dysfunction, as opposed to only "insulin resistance" from high levels of insulin and high blood glucose. It is clear that in the studies described above, elevated AHB in the context of baseline normoglycemia and non-dyslipidemia is diagnostic for increased likelihood of impaired beta cell function resulting in impaired first-phase insulin response. Again this is in contrast to the teachings of current literature which regards elevated AHB as a biomarker of impaired glucose disposal rates with utility for classifying patients on the continuum of insulin resistance towards T2DM.

It should be noted that in one study, when AHB was added to culture medium of an immortalized cell-line derived from beta cells, insulin secretion was suppressed. Conversely, when L-GPC was added to the same culture system, insulin secretion was stimulated. In our study, elevated plasma AHB even in the context of normal plasma L-GPC levels were predictive of impaired first phase response and significant post-prandial hyperglycemia. This suggests a dominant effect of AHB to suppress insulin secretion response even in the presence of potentiators such as L-GPC that work in vitro, which was not investigated or predicted by the in vitro study using cell lines. Furthermore, in the in vivo physiological milieu of the human organism, it is known that many substances from hormones to metabolites to toxins and drugs) may affect beta cell function and insulin secretion. For example, metabolites such as glutamate and GABA may be toxic to beta cells in vitro and in vivo (and these have been related to diabetes development and progression), and beta cells may be damaged by infections (e.g. enteroviral) and auto-immune processes as well. There are thus many factors interacting in a complex system in a human organism that contribute to beta cell health and number and secretory ability. Thus, the results shown in these examples could not have been predicted based on the current literature.

Preferred Embodiments

This invention comprises measurement of alpha-hydroxy butyrate (AHB) in blood or biological fluid of a fasted patient, wherein elevated levels of AHB compared to a healthy population or previous test values of a given patient are indicative of occult beta cell damage and predictive of impaired first-phase insulin response. The test may comprise measurement of AHB as a single analyte, and optionally other measurements of other biomarkers of glycemic control and/or dyslipidemia. In the one embodiment the test comprises measurement of alphahydroxybutyrate (AHB) alone. In a second embodiment, a panel of 3 core analytes may be used: alpha-hydroxybutyrate (AHB), and the ratio of triglycerides (trigs) to HDL-cholesterol (HDL-c). This invention requires only 1 baseline fasting blood sample. The sample is contacted and the amounts of the analytes are measured. A triglyceride to HDL-c ratio is calculated. An elevated amount of AHB (greater than about 4.5 µg/mL) measured in biological fluid from a fasting patient, particularly in a patient who is normoglycemic and/or non-dyslipidemic (defined as normal trig/HDLc ratio (less than 3)), indicates the presence of beta cell dysfunction and/or impaired first-phase insulin response, and thus enables said patient's risk level for progression to diabetes and the co-morbidities associated with development of diabetes to be determined. As an example, in an apparently normal individual, a baseline elevation of AHB greater than about 4.5 µg/mL would therefore cause the individual's risk to be increased from optimal to intermediate, or optimal to high.

The elevation of AHB in the context of normoglycemia and normal trig/HDL-c serves as a proxy for detection of the same individuals who have abnormally high elevations of 1-hour blood glucose (greater than 155 mg/dl) and impaired first-phase insulin response (which is indicative of beta cell dysfunction due to suppression or pancreatic islet damage). Because this test is able to identify a subset of at-risk patients currently missed by standard diagnostic techniques, these patients can be treated earlier such that the onset of forms of diabetes likely to require eventual treatment with exogenous insulin can be delayed or prevented by lifestyle and diet modifications, as well as pharmacologic intervention.

Treatment options for patients identified at risk by this diagnostic method may comprise causing one or more of the following: increased frequency of follow-up, referral for OGTT including time points between baseline and 2 hours, and/or CLIX, repetition of tests for monitoring disease progression, lifestyle and diet changes, and treatment with agents to improve beta cell function such as DPP-4 inhibitors and/or GLP-1 agonists, agents to treat post-prandial glucose excursions, and/or administration of insulin. Treatment may further comprise not administering typical first-line drugs that would normally be used to treat insulin resistance with no beneficial effect on pancreatic beta cell function, such as metformin, or adding agents which protect and enhance beta cell function to a regimen including metformin. Because the various embodiments of this test are proxies for decreased first-phase insulin response in response to glucose load of an OGTT, treatment may also comprise causing patient referral for comprehensive testing for development of Type-1 diabetes, such as tests for auto-antibodies to pancreatic islet beta cell antigens or other biomarkers of autoimmune disease (e.g. rheumatoid factor as a non-limiting example), and/or viral DNA/RNA and/or antibodies to viral capsid proteins for members of the enterovirus family that are known to cause pancreatic beta cell death and/or impairment of function. In the case of patients who are presumptively positive for any degree of enteroviral infection, and/or Type-1 Diabetes, and/or LADA, the treatment may comprise administering one or more of the following: an anti-viral agent, an immunosuppressant, insulin or an insulin analog, agents known to those skilled in the art to preserve beta cell function, agents that prevent post-prandial glucose excursions (e.g. Cycloset), and lifestyle and diet changes commonly prescribed for avoidance of development of Type 2 diabetes such as low-carbohydrate diets. Treatment may further comprise causing the avoidance of drugs or agents known to damage pancreatic islet cells.

Other treatments to reduce or ameliorate cardiovascular risk (cardiodiabetes) based on the results of this test further comprise contacting the patient sample, measuring the analytes included on HDL's panel tests for dyslipidemia, inflammatory biomarkers, and/or other biomarkers of cardiovascular disease, and determining the associated risk levels (optimal, intermediate, or high) for one or more of these analytes, and recommending appropriate risk-reduction therapy based on said determining. Therapy may comprise causing treatment with agents or lifestyle/diet changes for the improvement of these conditions. This improved risk stratification for future cardiodiabetes morbidity and mortality allows for therapeutic strategies such as those listed above, but not limited to those listed above, to be prescribed in order to ameliorate risk of development of cardiodiabetes and improvement of disease condition in existing cardiodiabetes.

The test panel may be used once, or repeatedly, for initial diagnosis of occult pancreatic beta cell dysfunction and/or for monitoring disease progression and/or for monitoring response to treatment. The biological sample is contacted, tested by means known to those skilled in the art, and the results are measured and reported to a qualified healthcare provider and/or patient. The report may take the form of a written report, a verbal discussion, a faxed report, or an electronic report accessed by a computing device or hand-held smart-phone device. A diagnostic and therapeutic nomogram based on the initial analyte measurements and the corresponding risk levels as well as other incidental laboratory test values and patient history, and comments may be added to the report based on this diagnostic nomogram that aid in data interpretation, diagnosis, and choice of therapy. Qualified healthcare provider is defined as a physician (MD, DO), nurse, registered dietician, pharmacist, or other appropriately trained individual qualified to counsel patients on health-related issues.

Beyond use of the test described herein to detect occult beta cell dysfunction and identify patients likely to display impaired first phase insulin response and progress to full-blown diabetes, additional biomarkers may be added to further improve diagnostic sensitivity/specificity and detection of and/or determination of risk of developing T1DM and the future cardiodiabetes complications. Short term post-prandial glucose elevations such as those demonstrated in patients with impaired first-phase insulin response are a known risk factor for development of many cardiodiabetic complications. As a non-limiting examples, biomarkers from the group comprising 1,5-AG, auto-antibodies related to type-1 diabetes, viral nucleic acids, antigens and/or antibodies to viral capsid proteins, biomarkers of dyslipidemia, metabolites related to the altered metabolism resulting from oxidative stress, and inflammatory biomarkers may be measured in addition to the core analytes previously described to further improve determination of patient risk level. In some embodiments only measurements of the core diagnostic analytes are used to classify patients' risks of progression as being optimal, intermediate, or high. In other embodiments the core analytes plus one or more additional analytes may be used to classify patients as optimal, intermediate, or high. In some cases a score may be calculated based on the measurement of core analytes plus additional analytes, and the mathematically derived score may be utilized to determine patient risk level, and said determining shall be used to guide treatment decisions.

In the preferred embodiment, the biological sample contacted is a blood component (serum or plasma). In other embodiments, other biological fluids comprising urine, saliva, or a combination of any biological fluids, may be contacted, and measurements of the analytes determined. It will be understood that all analytes need not be measured in the same fluid, i.e. 1,5 AG may be measured in urine or plasma and viral genetic material or proteins may be measured in cellular material, regardless of the biological sample type in which the other analytes are measured.

There have been no previous studies or reports in the literature of a test based on AHB alone or in combination with other analytes useful for predicting a priori which patients who are apparently normoglycemic (NGT) with apparently normal pancreatic beta cell function, are more likely to have clinically significant post-prandial glucose excursions greater than 155 mg/dl at 1 hour time point, and who are therefore at increased risk of cardiodiabetic complications. This novel test enables re-classification of "low- or optimal-risk" patients who would be considered normal by conventional diagnostics to be re-assigned to a higher risk category based on baseline elevations of AHB alone or in combination with other analytes. Taken together, the low insulin and elevated blood glucose at the "halfway point" of an OGTT are indicative of impaired beta cell function that is undetectable in the fasting state using conventional screening test methods. This test is unique in its ability to identify via elevated AHB, at a fasting baseline time point, the normoglycemic, normo-insulinemic, non-dyslipidemic patients who would be missed by existing diagnostic techniques who have impaired beta cell function sufficient to cause a decreased first-phase insulin response, and who are therefore at higher risk of beta cell exhaustion and progression to an insulin-dependent form of diabetes mellitus (IDDM) in the future. Because some forms of diabetes, such as LADA, may follow a relapsing/remitting pattern common to other auto-immune diseases, measuring baseline AHB will provide a means to monitor deterioration or improvement of pancreatic function and response to therapy even in intermediate forms of diabetes.

The measurement of AHB at baseline, without or without additional baseline analytes, allows for the identification of patients who have impaired beta cell function who would not be detected using the conventional diagnostic analytes (glucose, HbA1c, and insulin) at baseline. Because measurement of AHB at baseline reliably predicts which patients have beta cell dysfunction/impaired first phase response, OGTTs may be avoided in some cases. This would result in fewer blood samples being drawn from the patient due to elimination of multiple time points, a shorter time to obtain samples (no 2-hour waiting period for patient), fewer analytes needing to be measured, lower testing costs, shorter turn-around times for laboratory test results, no additional calculations needed such as CLIX scores to interpret data, and no need to account for impairment of kidney function (creatinine, eGFR). Measurement of elevated AHB can reclassify patients who are apparently low-risk to intermediate or high-risk of developing future cardiodiabetic disease due to beta cell dysfunction.

Examples

Figure 4:
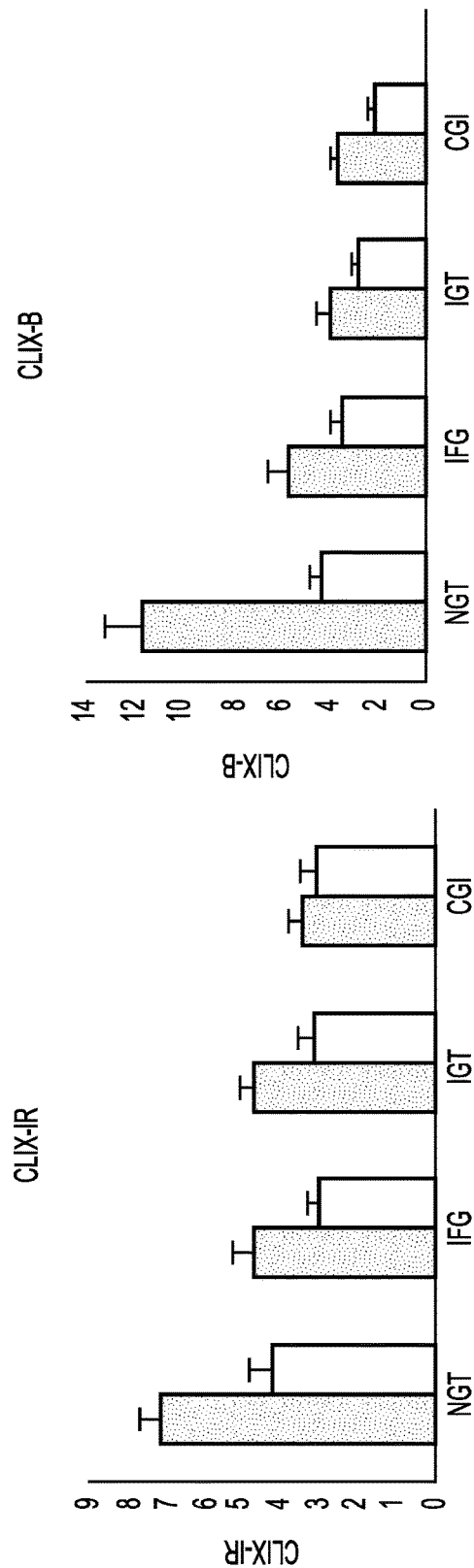
FIG. 4 shows CLIX-IR and CLIX-B graphs for patients assigned within each of the glycemic status (NGT, IFG, IGT and CGI).

Study No. 1:

A study was done wherein 100 patients were sampled at baseline (fasting) and again at 30 minutes, 1 hour, 90 minutes, and 2 hours post glucose load in an OGTT. Analytes listed in FIGS. 1-4 were measured. For each figure, glycemic status of the each patient was categorized into NGT, IFG, IGT, and CGI according to standard guidelines issued by the American Diabetes Association (see DIABETES CARE, vol. 20, sup. 7, July 1997). The figures then show whether the 1 hour glucose was above or below 155 mg/dL, which is the cutoff value established in the literature as a post-prandial hyperglycemic excursion value associated with increased risk of diabetes and resulting cardio-diabetic complications; this 1 hour cutoff value is further associated with decreased first phase insulin secretion response due to occult beta cell dysfunction in NGT individuals (see Abdul-Ghani and DeFronzo, DIABETES CARE, vol. 32, sup. 2, November 2009). CLIX scores were calculated based on the measured analytes, as a measure of insulin sensitivity. Patients were assigned to a group based on their CLIX scores: Normal Glucose Tolerance (NGT), Impaired Fasting Glucose (IFG), Impaired Glucose Tolerance (IGT), and Complete Glucose Intolerance (CGI). As noted in the figures below, approximately 20% of normoglycemics at baseline will be detected as at-risk (insulin resistant) by CLIX scoring. See FIG. 4.

FIGS. 5-8 show the values of various markers measured in each patient within the four glycemic status category and with 1-hour glucose cutoff distinctions. A marker that effectively predicts occult beta cell dysfunction will have a large value for the NGT red bar (high 1-hour glucose, the indication of beta cell dysfunction) and a low value for the NGT blue bar (regular 1-hour glucose).

Individual biomarkers measured at baseline were then studied to determine how well they would be able to predict which patients would have blood glucose elevated above 155 mg/dl at one hour, a value which has been associated in the literature and in longitudinal clinical studies (Botnia, SAHS) to be associated with development of diabetes and cardiodiabetic complications in the future. 1 hour glucose levels also strongly stratified risk within each traditional GTT glycemic category (Abdul-Ghani, et. al, 2008, 2009).

Figure 5:
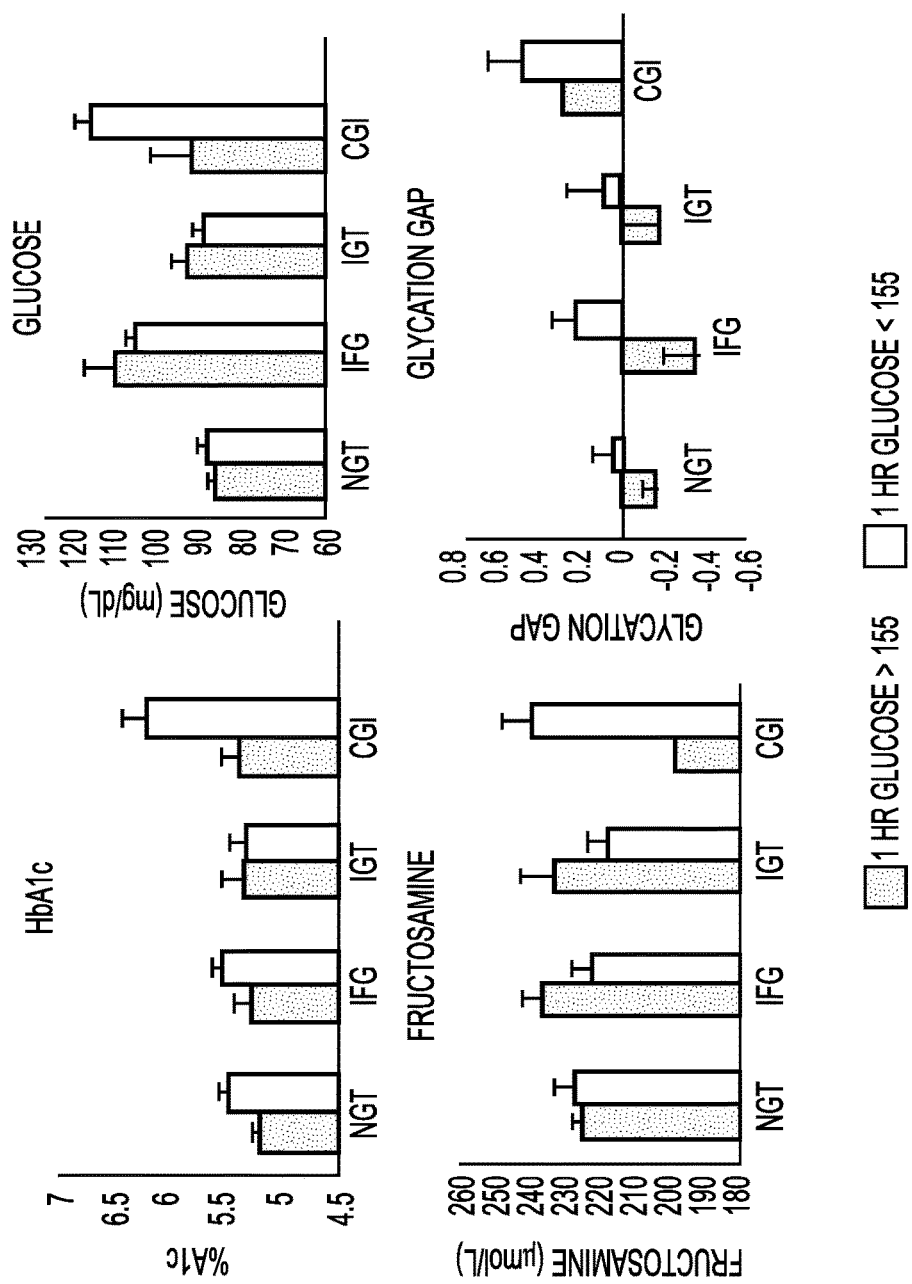
FIG. 5 shows graphs of biomarker levels for hemoglobin A1c, glucose, fructosamine and glycation gap for patients assigned within each of the glycemic status (NGT, IFG, IGT and CGI).
Figure 6:
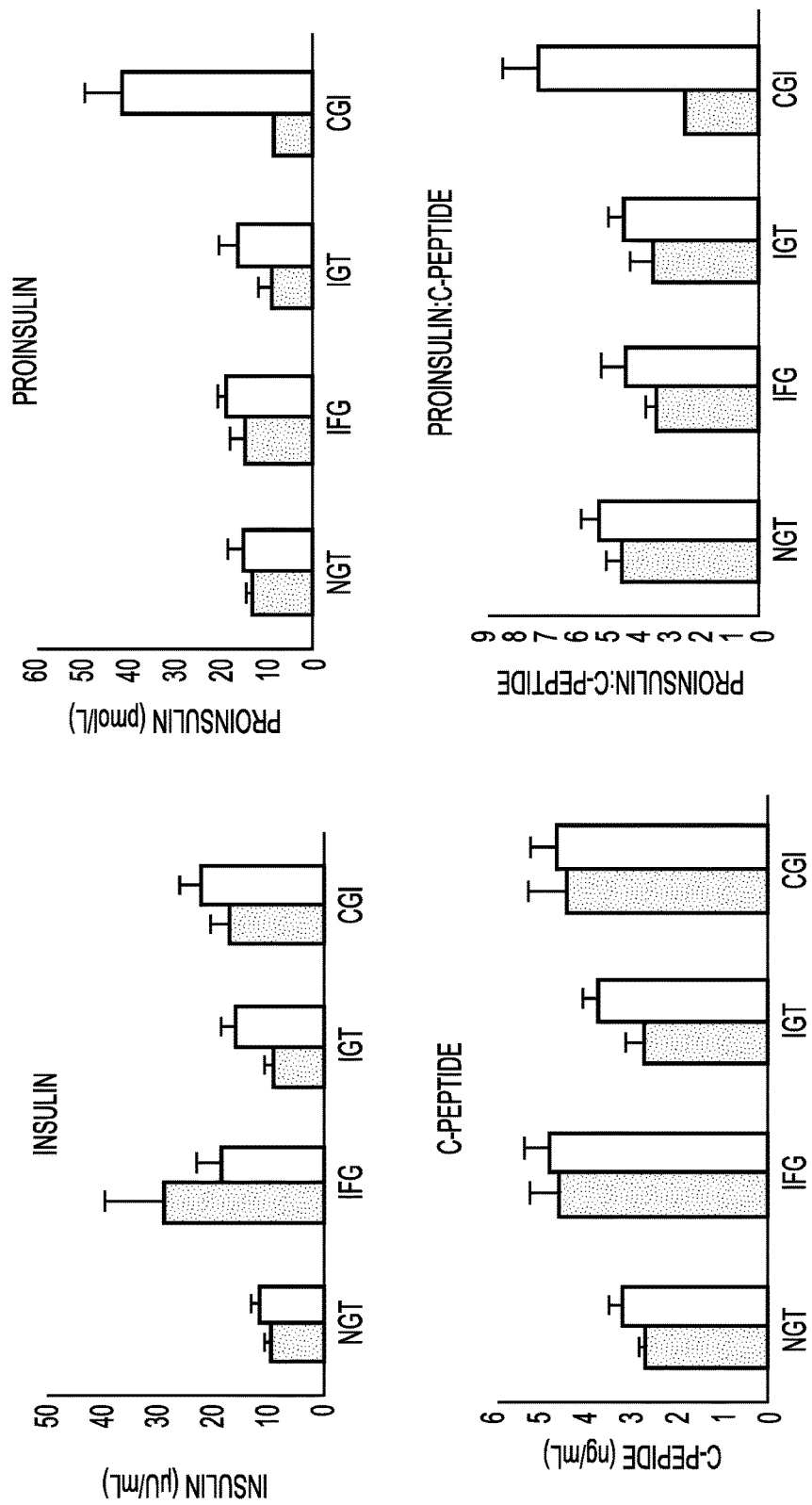
FIG. 6 shows graphs of biomarker levels for baseline insulin, pro-insulin, c-peptide and pro-insulin:c-peptide ratio for patients assigned within each of the glycemic status (NGT, IFG, IGT and CGI).
Figure 7:
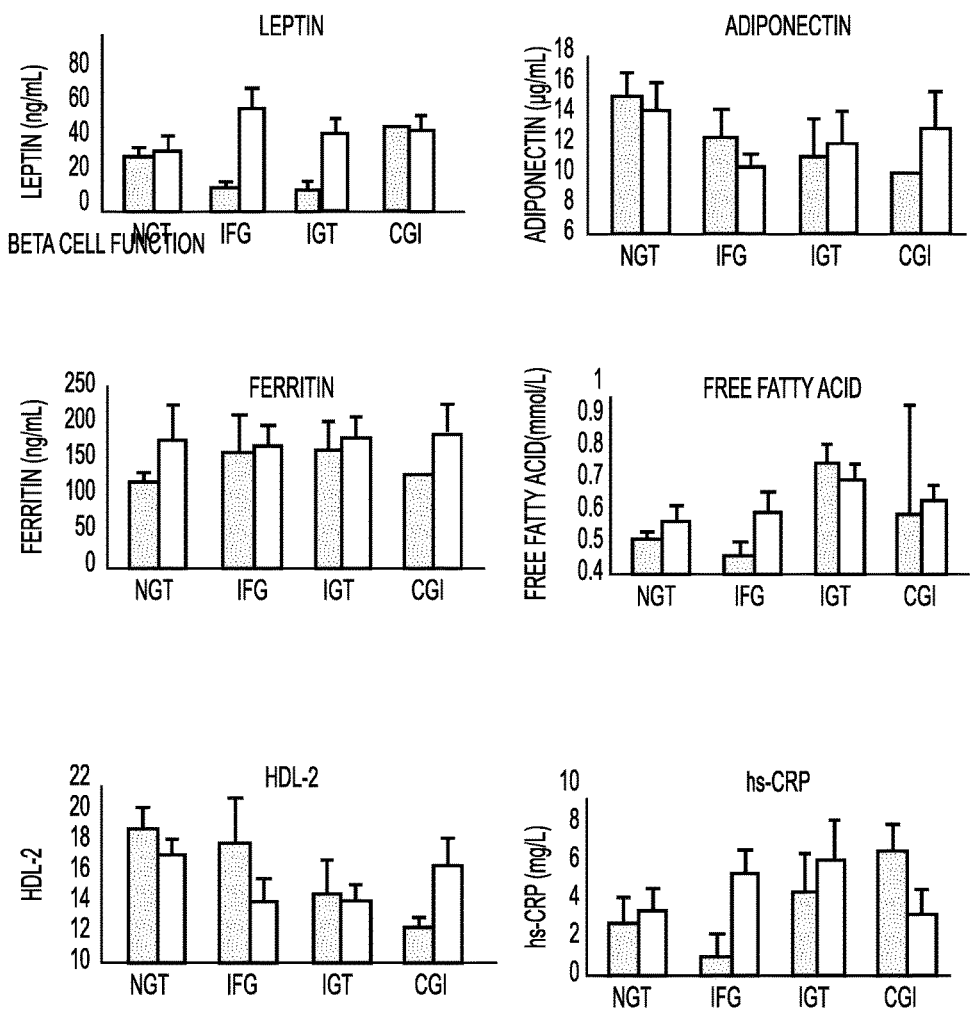
FIG. 7 shows graphs of biomarker levels for leptin, adiponectin, ferritin, free-fatty acid, HDL-2 and hs-CRP for patients assigned within each of the glycemic status (NGT, IFG, IGT and CGI).

FIG. 5 shows the lack of predictive power of common diagnostic tests for diabetes, namely HbA1c, Glucose, Fructosamine, and Glycation Gap. FIG. 6 shows the lack of predictive value of baseline insulin, pro-insulin, c-peptide, and proinsulin:c-peptide ratio. FIG. 7 shows the lack of predictive power for leptin, adiponectin, ferritin, free fatty acid, HDL-2, and hs-CRP.

Other biomarkers used to quantify insulin resistance, namely alpha hydroxybutyrate, Linoleoyl-GPC, Oleic Acid, IRI Score, HOMA-IR score, and LP-IR score were further studied. AHB in isolation was the only single biomarker that had significant predictive power for classifying which NGT patients would have blood glucose above 155 at 1 hour.

Figure 8:
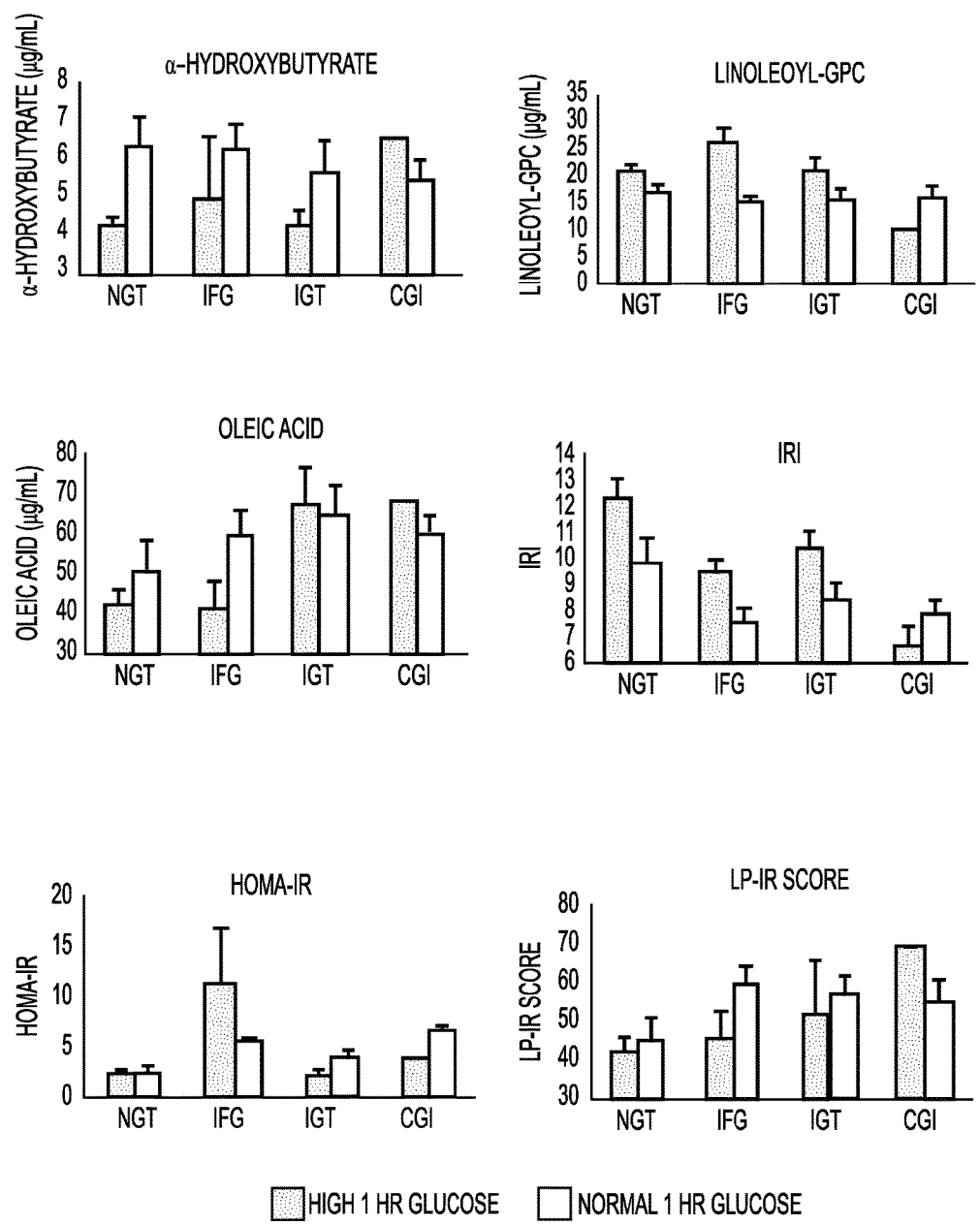
FIG. 8 shows graphs of biomarker levels for alpha-hydroxybutyrate (AHB), linoleoyl-GC, oleic acid, IRI, HOMA-IR and LP-IR score for patients assigned within each of the glycemic status (NGT, IFG, IGT and CGI).

FIG. 8 shows a lack of predictive value for common biomarkers Linoleoyl-GPC, Oleic Acid, HOMA-IR and LP-IR Score. AHB (a-hydroxybutyrate) shows strong predictive power in this figure. IRI score, which incorporates measurement of AHB, L-GPC, Oleic Acid, and a mathematical weighting by either BMI (in this study) or baseline insulin (formula currently in clinical diagnostic use) also shows statistically relevant results, however, the score's weighting by BMI limits its clinical utility to detection of patients with significant insulin resistance in the context of metabolic syndrome and/or hyper-insulinemia and dyslipidemia.

Figure 9:
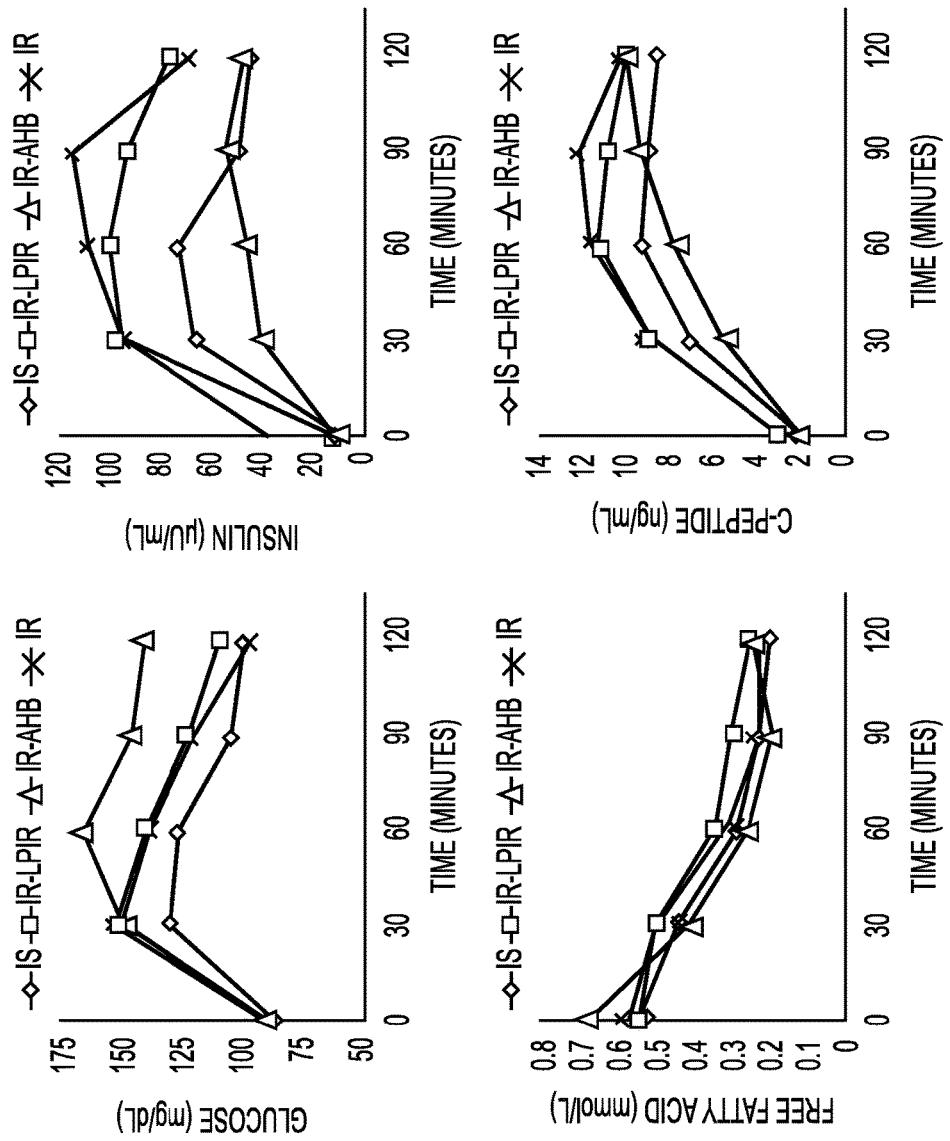
FIG. 9 shows graphs of biomarkers levels for glucose, insulin, free fatty acids and c-peptide for NGT patients assigned to the following categories: insulin sensitive (IS), insulin resistant (IR) by high baseline trig/HDLc ratio only, IR by high baseline AHB only or IR by both trig/HDLc, and AHB high at baseline.

In FIG. 9, the NGT patients were assigned to categories of IS (insulin sensitive), IR (insulin resistant) by high baseline trig/HDLc ratio only, IR by high baseline AHB only, or IR by both trig/HDL-c and AHB high at baseline. The levels of Glucose, Insulin, Free Fatty Acids, and C-peptide at each of the time points in the study were then compared for each of these groups. In the upper left panel, there is a clear difference between 1 hour glucose actually measured between the IS group (AHB not elevated at baseline, blue) and the IR-AHB group (only AHB elevated at baseline, green). The group with only elevated baseline AHB has significantly higher 1 hour blood glucose than the IS controls, demonstrating the utility of this biomarker as a proxy for 1 hour glucose measurements. In the upper right panel, it can be clearly seen that by 1 hour the insulin secretion in the group with elevated baseline AHB was markedly lower than controls, demonstrating that 1) the ability of the pancreatic beta cell to secrete insulin in response to a glucose challenge is impaired, and 2) this less than optimal insulin secretion may be the cause of the elevated blood glucose values at 1 hour in this group.

This line of evidence is further reinforced by data on blunted C-peptide secretion (FIG. 9 bottom right panel) in the group with elevated baseline AHB. C-pep is released when pro-insulin is cleaved to insulin and declining levels of C-pep and increased pro-insulin to C-pep ratio is associated with a decline in beta cell function. The abnormally low levels of C-pep at 1 hour post-glucose challenge correspond to the abnormally low insulin levels and serve as confirmation that there is indeed less insulin secreted in the NGT group with elevated baseline AHB. Because elevated AHB only, at baseline, in normoglycemic non-dyslipidemic subjects, is able to predict which patients will have impaired insulin secretion and therefore 1 hour post-challenge glucose excursions, it has clinical utility in identifying patients that would normally be mis-classified as normal and at low risk of developing diabetes and reclassifying them properly into a category of increased risk. The data trends shown in FIG. 9 support the conclusion that elevated baseline AHB is strongly associated with beta cell dysfunction and impaired first phase insulin response.

It is also worth noting in FIG. 9 that all of the patients were tested for anti-GAD antibody, which is the most common auto-antibody to pancreatic beta cells in Type 1 diabetics. All of the patients were negative for anti-GAD, which is significant because impaired insulin secretion on glucose challenge could be indicative of the presence of Type 1 diabetes. However, just because the patients were negative for the most common auto-antibody detected in Type 1 diabetics does not mean that they are not early-stage Type 1's or LADAs (Latent Autoimmune Diabetes in Adults) or suffering from Insulin Auto-immune Syndrome (IAS) wherein the body produced auto-antibodies to insulin that can also result in slow progression to insulin-dependent diabetes. IAS patients typically have hypoglycemic episodes and normal or low-normal insulin levels at baseline, meaning that the standard tests for glycemic control such as HbA1c, fructosamine, and glycation gap would be normal and not raise any suspicion of presence of IAS until it progresses to abnormally low levels of insulin and pancreatic beta cell dysfunction sufficient to cause symptoms.

So it is possible that some of the patients with elevated baseline AHB who exhibit abnormally low insulin levels and abnormally high glucose levels at 1 hour in an OGTT could be positive for one of the other autoantibodies detectable in Type 1 diabetics that HDL did not test for, or they may have occult damage to their pancreatic beta cells from a past or current viral infection, such as enterovirus infections, that is/was not severe enough to be detected at baseline and is only observable when the patient is challenged with a glucose load in an OGTT.

Figure 10:
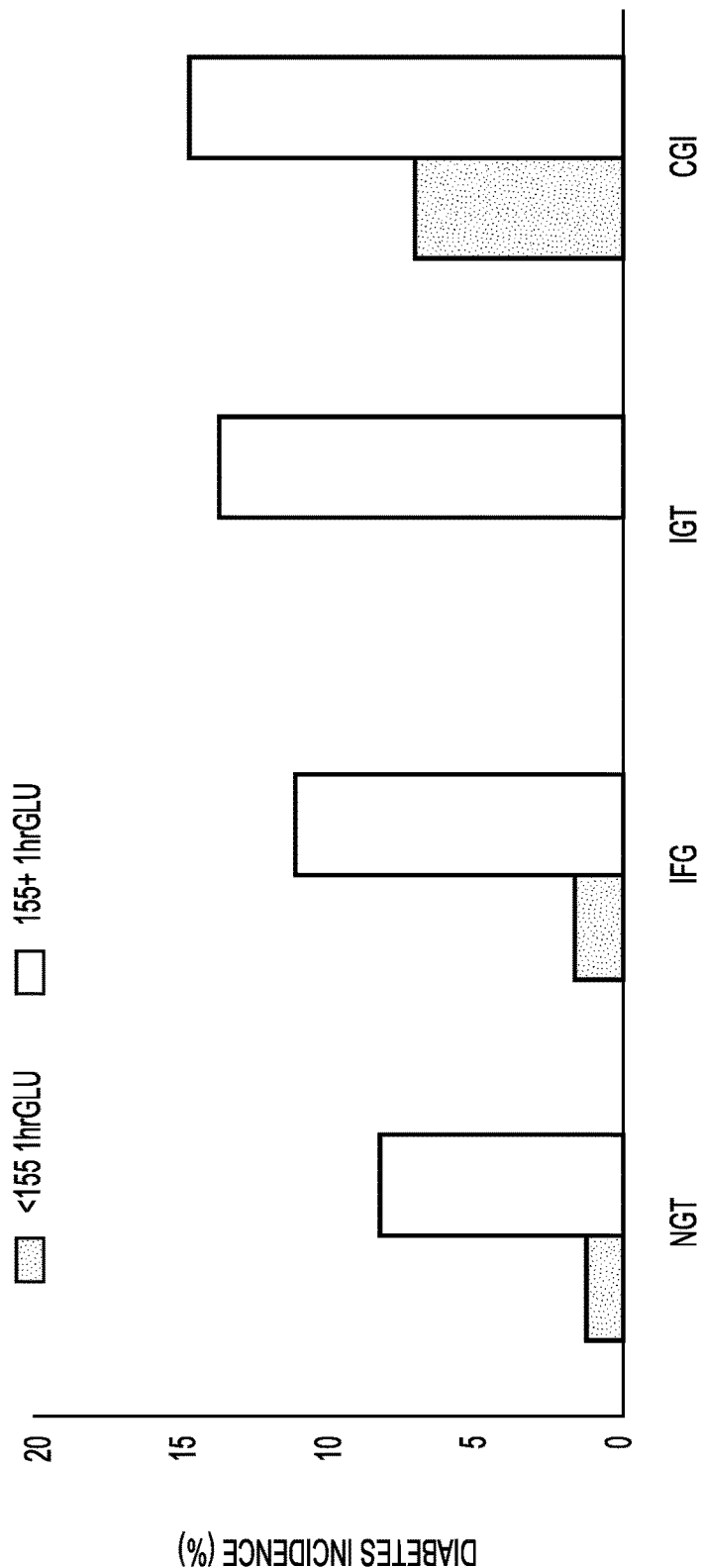
FIG. 10 is a graph depicting 1-hour glucose values measured against traditional GTT glycemic categories. The graph shows that a 1-hour glucose value of above 155 mg/dL was strongly associated with diabetes incidence in the Botnia and SAHS studies (during 8 years of f/u). Adapted from Abdul-Ghani et al., 2009.

Additional validation of the 1 hour glucose levels as a marker for future diabetes risk is presented in FIG. 10. The data show that a 1-hour glucose level of 155 mg/dL or higher is strongly associated with diabetes incidence in the Botnia and SAHS (San Antonio Heart Study). It is noted that the 1-hour glucose reading strongly stratified risk within each traditional GTT glycemic category (see Abdul-Ghani and DeFronzo DIABETES CARE, vol. 32, sup. 2, November 2009).

Study No. 2:

OGTTs with multiple time points were performed on 222 subjects. Patients with any signs of impaired glucose tolerance, or T1DM were excluded per the table below (Table 1), leaving a total of 87 subjects who were normoglycemic and normo-insulinemic. Patient population was mixed sex, mixed race, various ages, and on various medications. This was an "all-comers" study to test the strength of the predictive power of AHB in an apparently normal population.

TABLE 1

| Define non-insulin resistant subjects | |
|---|---|
| Condition (in order) | N |
| All oral glucose tolerance tests with AHB | 222 |
| AntiGad > 5 | 6 |
| Insulin 0 hr > 12 | 78 |
| Glucose 0 hr ≥ 100 | 20 |
| Glucose 2 hr ≥ 140 | 17 |
| HbA1c missing | 6 |
| HbA1c ≥ 5.7 | 6 |
| Glucose 1 hr missing | 1 |
| BMI missing | 1 |
| Total sample size | 87 |

There were 87 subjects that were not insulin resistant by current clinical definitions (Table 1). The mean (SD) glucose elevation above baseline at 1-hour was 33(34) mg/dL. The relationship between the 1-hour glucose 'bump' and alpha-hydroxybutyrate (AHB) was linear over the range 1.7 to 12.2 ug/mL (FIG. 11).

Figure 11:
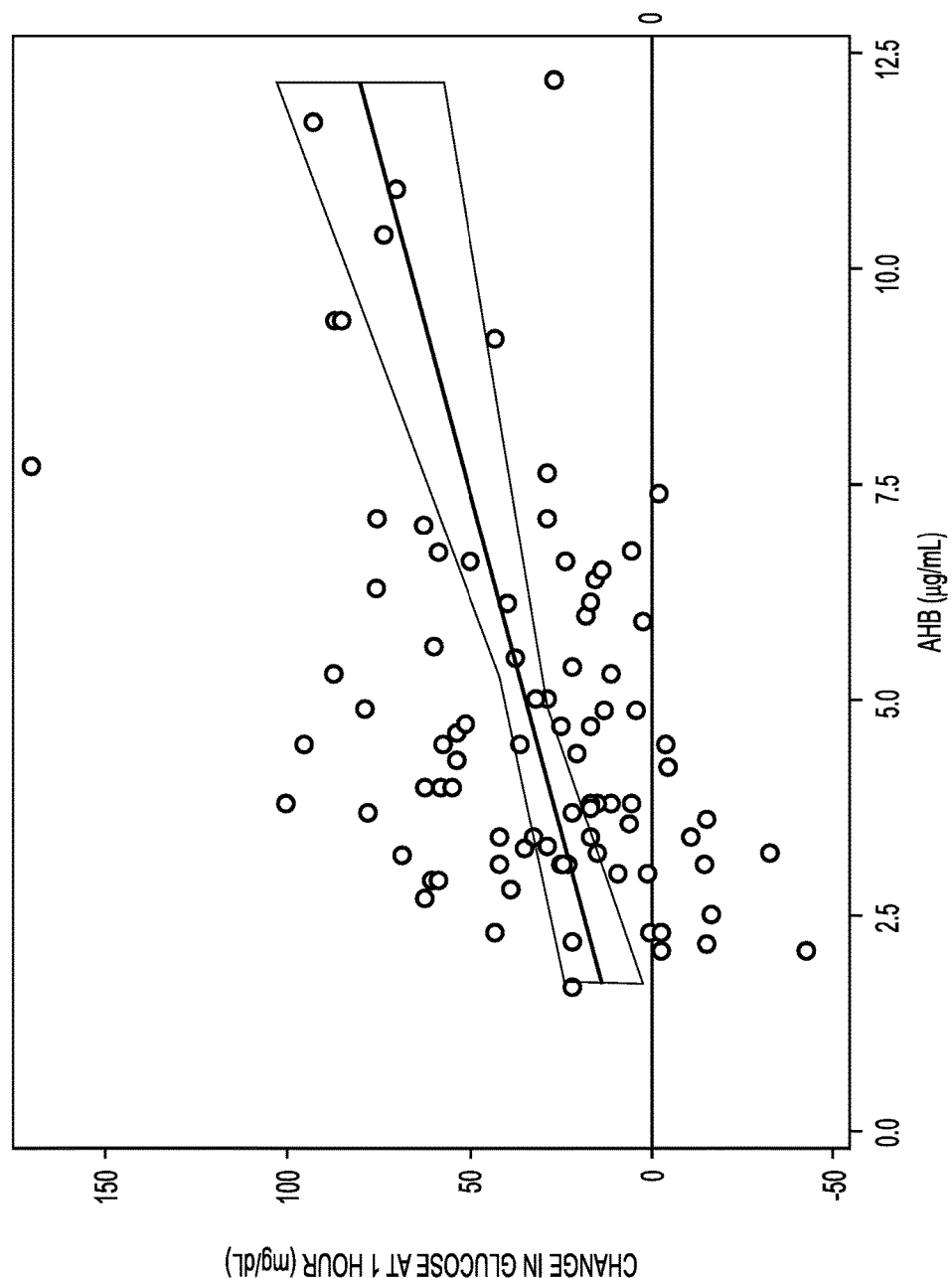
FIG. 11 is a graph showing a linear relationship between a one (1)-hour glucose "bump" (mg/dL) and AHB (μg/mL) over the range 1.7 to 12.2 μg/mL in 87 normoglycemic and normo-insulinemic subjects tested.

FIG. 11 shows that AHB predicts a change in glucose at 1-hour using linear regression with 95% mean confidence band. Each 1 ug/mL increase in fasting AHB was correlated with 6.4 mg/dL higher 1-hour glucose levels (p<0.0001) following an oral glucose tolerance test (Table 2). Furthermore, the variability in AHB explained about 16% of the variability in elevated 1-hour glucose levels. Per these results, if a subject is just below a fasting glucose of 100 mg/dL, then a mean 55 mg/dL elevated 1-hour glucose would equate to an AHB of 8.2 ug/mL. This relationship between AHB measurement and 1-hr glucose held regardless of age, gender, or baseline glucose levels (Tables 3 & 4, FIG. 12).

The strength of the relationship between AHB and elevated 1-hour glucose levels remained, but was slightly attenuated in subgroups of the healthiest patients. One of these subgroups was defined by reducing the baseline insulin level to ≤9 for inclusion. Then a 1 unit increase in AHB was correlated with 5.3 mg/dL higher 1-hour glucose levels (p=0.0044, N=69). The healthiest patients were also defined by excluding dyslipidemias measured by triglyceride to HDL cholesterol ratio (Tg/HDLC) or LP-IR score. When subjects with Tg/HDLC ≥3 were excluded, then a 1 unit increase in AHB was correlated with 5.1 mg/dL higher 1-hour glucose levels (p=0.0031, N=61). Similar results were obtained when subjects with LP-IR >50 were excluded, then a 1 unit increase in AHB was correlated with 4.3 mg/dL higher 1-hour glucose levels (p=0.027, N=52).

Fasting AHB levels were also used to predict the probability of having a 1-hour glucose level ≥155 mg/dL. For each 1 unit increase in AHB a patient was 1.6 times as likely to have levels above this threshold (Table 5, p=0.0005). Also the model fit was calibrated across risk deciles of having an elevated 1-hour glucose (Hosmer-Lemeshow p=0.99). AHB was effective in discriminating patients; the area under the ROC curve was 0.79 for AHB alone, which was greater than chance (p<0.0001, FIG. 12).

Figure 12:
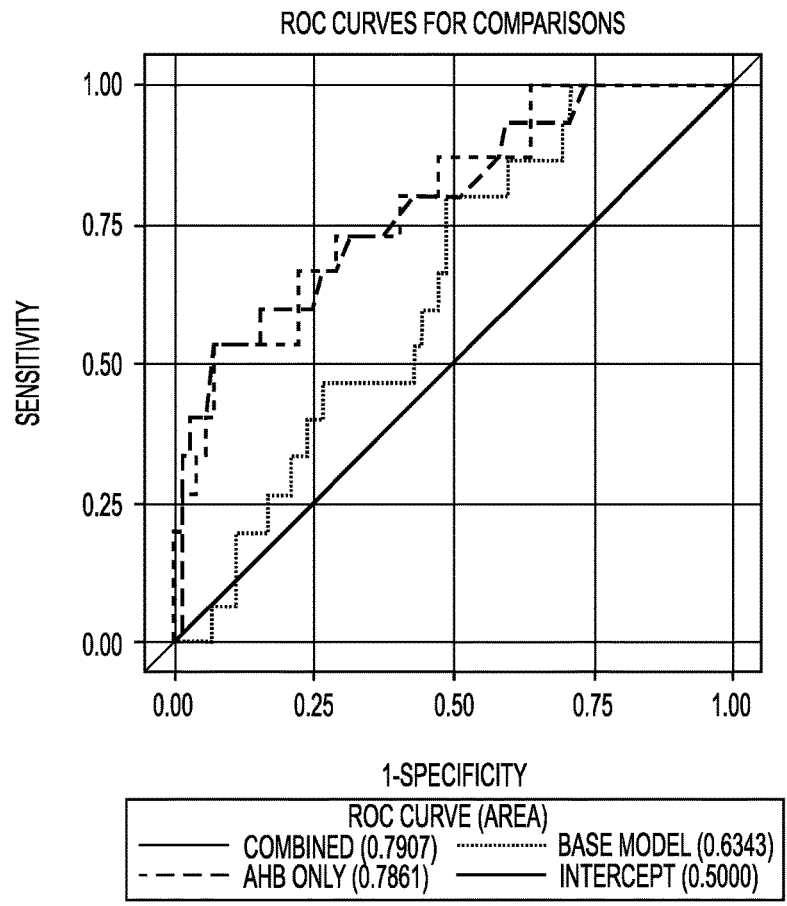
FIG. 12 shows an ROC curve comparing the relationship between AHB measurement and one (1)-hour glucose held regardless of age, gender or baseline glucose levels.

FIG. 12 shows discrimination of patients with 1-hour glucose ≥155 mg/dL. In that figure the base model included age, gender, BMI, and baseline glucose. Adding AHB to a model with age, baseline glucose and gender increased the AUC from 0.62 to 0.79 (p=0.027). The sum of sensitivity and specificity were at a maximum with an AHB cut point ≥6.8; 53% and 93%, respectively (Table 12). This resulted in a positive likelihood ratio (PLR) of 7.8, which meant a patient with an AHB ≥6.8 was almost 8 times as likely to have a 1-hour glucose ≥155 mg/dL. A good clinical test has a PLR >3 and an excellent test has a PLR >6.

These data are evidence that fasting alpha-hydroxybutyrate is an effective risk marker for elevated glucose levels at 1-hour following an oral glucose tolerance test. The results are consistent when 1-hour glucose levels are modeled continuously or dichotomously using a known threshold (≥155 mg/dL) of increased risk for development of cardiodiabetic diseases.

TABLE 2

AHB predicts change in 1-hour glucose using linear regression

Analysis of Variance

| Source | DF | Sum of Squares | Mean Square | F Value | Pr > F |
|---|---|---|---|---|---|
| Model | 1 | 17481 | 17481 | 18.08 | <.0001 |
| Error | 86 | 83172 | 967.11064 | | |
| Corrected Total | 87 | 100652 | | | |

| Root MSE | 31.09840 |
|---|---|
| Dependent Mean | 33.36364 |
| Coeff Var | 93.21047 |
| R-Square | 0.1737 |
| Adj R-Sq | 0.1641 |

TABLE 2-continued

AHB predicts change in 1-hour glucose using linear regression

Parameter Estimates

| Variable | DF | Parameter Estimate | Standard Error | t Value | Pr > |t| |
|---|---|---|---|---|---|
| Intercept | 1 | 2.52508 | 7.97521 | 0.32 | 0.7523 |
| AHB | 1 | 6.37190 | 1.49874 | 4.25 | <.0001 |

TABLE 3

AHB predicts change in 1-hour glucose using linear regression model adjusted for age, gender, baseline glucose and their interactions with AHB. AHB, age, and glucose were mean centered.

Analysis of Variance

| Source | DF | Sum of Squares | Mean Square | F Value | Pr > F |
|---|---|---|---|---|---|
| Model | 7 | 20675 | 2953.54743 | 2.95 | 0.0083 |
| Error | 80 | 79978 | 999.71915 | | |
| Corrected Total | 87 | 100652 | | | |

| Root MSE | 31.61834 |
|---|---|
| Dependent Mean | 33.36364 |
| Coeff Var | 93.76885 |
| R-Square | 0.2054 |
| Adj R-Sq | 0.1359 |

Parameter Estimates

| Variable | DF | Parameter Estimate | Standard Error | t Value | Pr > |t| | Variance Inflation |
|---|---|---|---|---|---|---|
| Intercept | 1 | 33.49188 | 4.69663 | 7.13 | <.0001 | 0 |
| ahb_cl | 1 | 6.26981 | 2.41269 | 2.60 | 0.0111 | 2.50697 |
| age_cl | 1 | 0.01641 | 0.24530 | 0.07 | 0.9468 | 1.06289 |
| gluc0_cl | 1 | 0.08321 | 0.48601 | 0.17 | 0.8645 | 1.07353 |
| Male | 1 | 0.29552 | 6.96140 | 0.04 | 0.9662 | 1.05763 |
| ahb_age | 1 | 0.15014 | 0.12292 | 1.22 | 0.2255 | 1.40144 |
| ahb_gluc0 | 1 | 0.13073 | 0.25092 | 0.52 | 0.6038 | 1.30816 |
| ahb_male | 1 | -0.04190 | 3.51283 | -0.01 | 0.9905 | 2.82172 |

TABLE 4

AHB predicts change in 1-hour glucose using linear regression model adjusted for age, gender, and baseline glucose.

Analysis of Variance

| Source | DF | Sum of Squares | Mean Square | F Value | Pr > F |
|---|---|---|---|---|---|
| Model | 4 | 17569 | 4392.14936 | 4.39 | 0.0029 |
| Error | 83 | 83084 | 1001.00923 | | |
| Corrected Total | 87 | 100652 | | | |

| Root MSE | 31.63873 |
|---|---|
| Dependent Mean | 33.36364 |
| Coeff Var | 94.82998 |
| R-Square | 0.1745 |
| Adj R-Sq | 0.1348 |

Parameter Estimates

| Variable | DF | Parameter Estimate | Standard Error | t Value | Pr > |t| | Variance Inflation |
|---|---|---|---|---|---|---|
| Intercept | 1 | -3.47725 | 40.81224 | -0.09 | 0.9323 | 0 |
| AHB | 1 | 6.34436 | 1.53574 | 4.13 | <.0001 | 1.01443 |
| Age | 1 | 0.01727 | 0.24161 | 0.07 | 0.9432 | 1.02983 |
| GLUC0 | 1 | 0.05390 | 0.48127 | 0.11 | 0.9111 | 1.05134 |
| Male | 1 | 1.60269 | 6.89453 | 0.23 | 0.8168 | 1.03607 |

TABLE 5

AHB predicts 1-hour glucose > 155 mg/dL using logistic regression model adjusted for age, gender, and baseline glucose

Testing Global Null Hypothesis: BETA = 0

| Test | Chi-Square | DF | Pr > ChiSq |
|---|---|---|---|
| Likelihood Ratio | 17.9144 | 4 | 0.0013 |

Analysis of Maximum Likelihood Estimates

| Parameter | DF | Estimate | Standard Error | Wald Chi-Square | Pr > ChiSq |
|---|---|---|---|---|---|
| Intercept | 1 | −10.9372 | 4.7377 | 5.3294 | 0.0210 |
| AHB | 1 | 0.5007 | 0.1433 | 12.2000 | 0.0005 |
| Age | 1 | 0.0139 | 0.0239 | 0.3374 | 0.5613 |
| Male | 1 | 0.0484 | 0.6594 | 0.0054 | 0.9415 |
| GLUC0 | 1 | 0.0689 | 0.0518 | 1.7707 | 0.1833 |

Odds Ratio Estimates

| Effect | Point Estimate | 95% Wald Confidence Limits | |
|---|---|---|---|
| AHB | 1.650 | 1.246 | 2.185 |
| Age | 1.014 | 0.968 | 1.063 |
| Male | 1.050 | 0.288 | 3.822 |
| GLUC0 | 1.071 | 0.968 | 1.186 |

Hosmer and Lemeshow Goodness-of-Fit

| CHI-Square | DF | Pr > ChiSq |
|---|---|---|
| 1.5677 | 8 | 0.9915 |

The prior AHB results are supported in statistical models adjusted for age, gender, baseline glucose, and BMI (Tables 6 & 7, FIG. 12). The relations between AHB and various OGTT endpoints including glucose, insulin, C-peptide, and proinsulin are summarized in Table 8. The AHB slope estimates to 30-minute and 1-hour glucose excursion (FIGS. 5 & 6). AHB has the following results:

1) Linear relation with the 1-hour and 30-minute glucose measurement (Table 8, p<0.0009)
2) Associated with the probability of having a 1-hour glucose >155 mg/dL (Table 7, p=0.0005)
3) Association is calibrated across the range of data (Table 7, Hosmer-Lemeshow p=0.69)
4) AHB adds to the discrimination of subjects having a 1-hour glucose ≥155 mg/dL; the area under the ROC curve increases by 16% (FIG. 12, p=0.039) compared to a model with age, gender, BMI, and baseline glucose (FIG. 12).

Several variable selection methods were explored to determine if other variables could assist AHB in explaining variability in the 1-hour glucose 'bump' and classifying patients with 1-hour glucose ≥155 mg/dL. LGPC had a significant linear relation with the 1-hour glucose measurement (Table 9, p=0.038); however, it did not add any information to classifying subjects above the 155 mg/dL 1-hour threshold (Table 10, p=0.35).

Correlations were determined with AHB and FFA, CLIX-IR, CLIX-Beta Cell, CRP, and Lp-PLA2 (Table 11). Pearson correlations assume a bivariate normal distribution, such that at least both variables are normally distributed. These assumptions can be investigated using several methods; basic tools available are the skewness and kurtosis measures. As a rule-of-thumb when the absolute value of the skewness is greater than 3, or kurtosis is greater than 10, the normality assumption is not tenable. In these data the CLIX-Beta Cell measure had absolute skew=6.6 and kurtosis=44 (Table 11), which identified two outlier observations (FIG. 15). When normality is not reasonable and the variables are continuous measures, then Spearman's Rank correlation should be used instead. In these raw data, the Pearson's correlation for CLIX-Beta Cell with AHB was r=0.12, p=0.28. However, since the data are non-normal Spearman's correlation was a more accurate measure r=−0.30, p=0.0046. When the two outliers were removed, which may or may not be appropriate depending if they are viable measurements, then Pearson's correlation correctly identified the magnitude and direction of the linear relation, r=−0.32, p=0.00289 (Table 11).

These data are evidence that fasting alpha-hydroxybutyrate is an effective risk marker for elevated glucose levels at 30 minutes and 1-hour following an oral glucose tolerance test. The results are consistent when 1-hour glucose levels are modeled continuously or dichotomously using a known threshold (≥155 mg/dL) of increased risk for progression to diabetes. Using the current empirically determined HDL guidelines for AHB high risk level (i.e. >5.7 ug/mL), produces a positive likelihood ratio (PLR) of 3.1. This means a patient with an AHB >5.7 is about 3 times as likely to have a 1-hour glucose >155 mg/dL.

These results were not influenced by age, gender, BMI, or baseline glucose levels. These results were also not affected by any anti-diabetic medications, lipid altering medications, or fish oil. However, the medication status of 40 (45%) of the subjects was unknown. The strength of the relationship between AHB and elevated 1-hour glucose levels remained in subgroups of the healthiest patients defined as those without dyslipidemias measured by triglyceride to HDL cholesterol ratio (Tg/HDLC) or LP-IR score, or when lowering the level of fasting insulin from ≤12 to ≤9 for inclusion.

Figure 13:
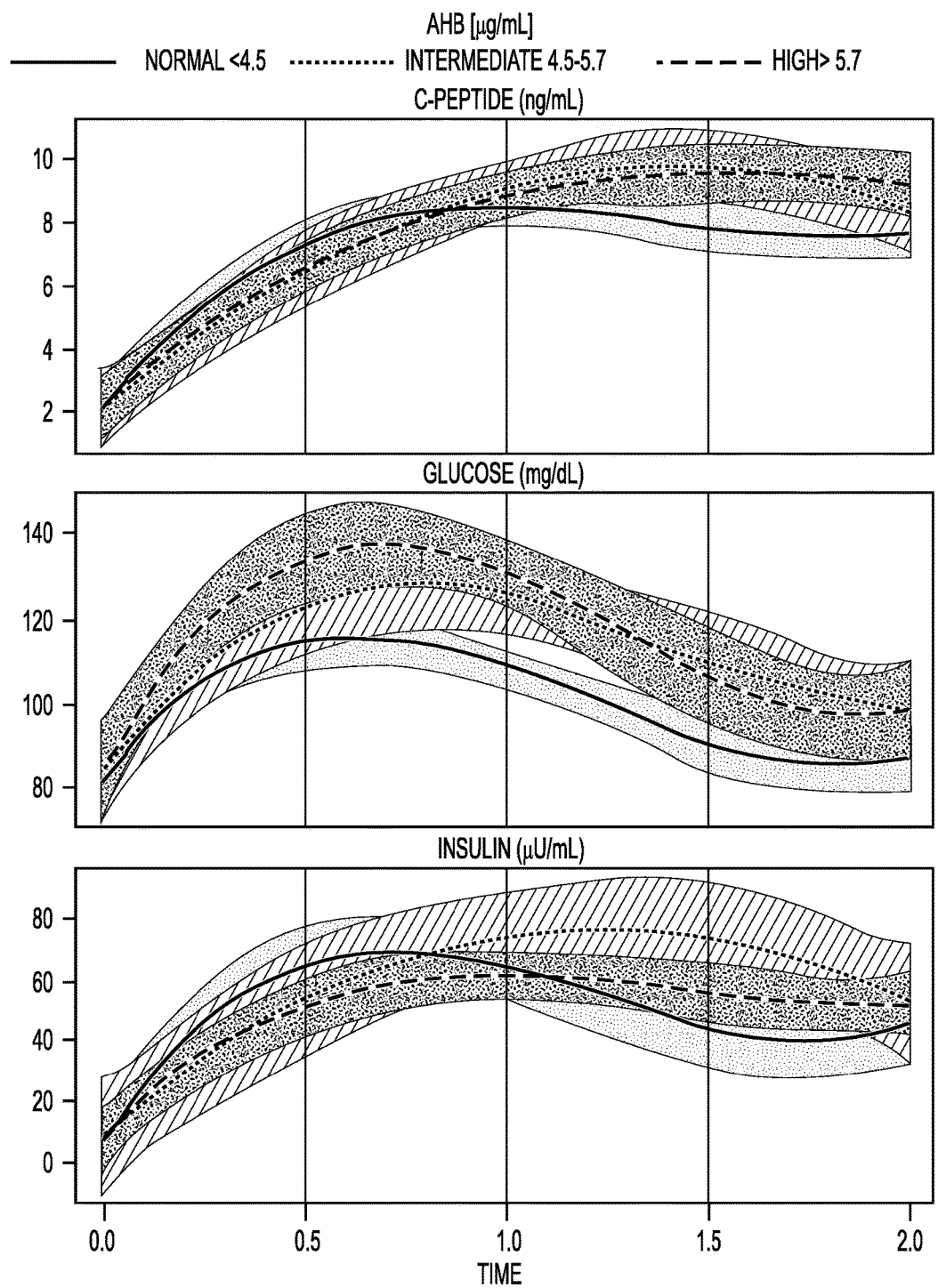
FIG. 13 shows oral glucose tolerance test (OGTT) response area under the curve (AUC) using cubic regression with 95% mean confidence bands by AHB levels (i.e., normal, intermediate, high).
Figure 14:
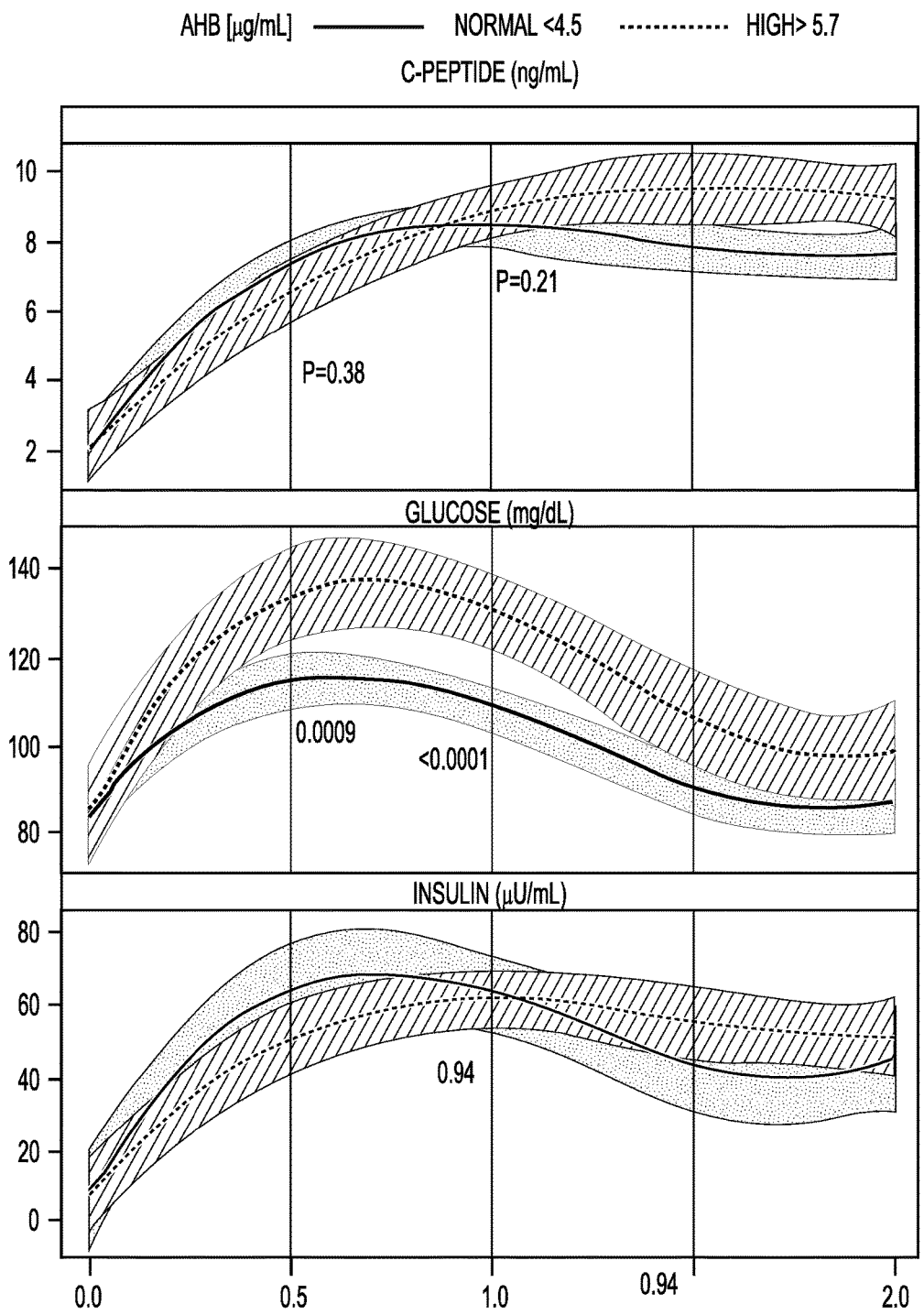
FIG. 14 shows oral glucose tolerance test (OGTT) response area under the curve (AUC) using cubic regression with 95% mean confidence bands by AHB levels (i.e., normal, high).

FIG. 13 shows oral glucose tolerance test responses using cubic regression with 95% confidence bands by AHB levels (i.e. normal, intermediate, high). FIG. 14 shows oral glucose tolerance test responses using cubic regression with 95% confidence bands by AHB levels (i.e. normal, high). FIG. 15 shows a distribution of beta cell CLIX score with extreme IDs=834498, 924352.

TABLE 6

AHB predicts change in 1-hour glucose using linear regression model adjusted for age, gender, BMI, and baseline glucose.

Analysis of Variance

| Source | DF | Sum of Squares | Mean Square | F Value | Pr > F |
|---|---|---|---|---|---|
| Model | 5 | 17402 | 3480.33690 | 3.44 | 0.0071 |
| Error | 81 | 81839 | 1010.35298 | | |
| Corrected Total | 86 | 99240 | | | |

TABLE 6-continued

AHB predicts change in 1-hour glucose using linear regression model adjusted for age, gender, BMI, and baseline glucose.

| | |
|---|---|
| Root MSE | 31.78605 |
| Dependent Mean | 33.79310 |
| Coeff Var | 94.06076 |
| R-Square | 0.1753 |
| Adj R-Sq | 0.1244 |

Parameter Estimates

| Variable | DF | Parameter Estimate | Standard Error | t Value | Pr > \|t\| | Variance Inflation | 95% Confidence Limits | |
|---|---|---|---|---|---|---|---|---|
| Intercept | 1 | −14.21410 | 43.89913 | −0.32 | 0.7469 | 0 | −101.55959 | 73.13140 |
| AHB | 1 | 6.28384 | 1.54464 | 4.07 | 0.0001 | 1.01576 | 3.21048 | 9.35720 |
| Age | 1 | 0.03713 | 0.24473 | 0.15 | 0.8798 | 1.04269 | −0.04269 | 0.52407 |
| GLUC0 | 1 | 0.12484 | 0.49249 | 0.25 | 0.8005 | 1.06678 | −0.85506 | 1.10474 |
| Male | 1 | 1.03406 | 7.10739 | 0.15 | 0.8847 | 1.08040 | −13.10741 | 15.17553 |
| BMI | 1 | 0.16036 | 0.57133 | 0.28 | 0.7797 | 1.05721 | −0.97642 | 1.29713 |

TABLE 7

AHB predicts 1-hour glucose ≥ 155 mg/dL using logistic regression model adjusted for age, gender, BMI, and baseline glucose Testing Global Null Hypothesis: BETA = 0

| Test | Chi-Square | DF | Pr > ChiSq |
|---|---|---|---|
| Likelihood Ratio | 17.9447 | 5 | 0.0030 |

Analysis of Maximum Likelihood Estimates

| Parameter | DF | Estimate | Standard Error | Wald Chi-Square | Pr > ChiSq |
|---|---|---|---|---|---|
| Intercept | 1 | −11.2959 | 4.9384 | 5.2319 | 0.0222 |
| AHB | 1 | 0.4978 | 0.1431 | 12.1004 | 0.0005 |
| Age | 1 | 0.0147 | 0.0240 | 0.3718 | 0.5420 |
| Male | 1 | 0.0116 | 0.6735 | 0.0003 | 0.9862 |
| GLUC0 | 1 | 0.0722 | 0.0526 | 1.8850 | 0.1698 |
| BMI | 1 | 0.00290 | 0.0546 | 0.0028 | 0.9576 |

Odds Ratio Estimates

| Effect | Point Estimate | 95% Wald Confidence Limits | |
|---|---|---|---|
| AHB | 1.645 | 1.243 | 2.178 |
| Age | 1.015 | 0.968 | 1.064 |
| Male | 1.012 | 0.270 | 3.787 |
| GLUC0 | 1.075 | 0.970 | 1.192 |
| BMI | 1.003 | 0.901 | 1.116 |

Hosmer and Lemeshow Goodness-of-Fit Test

| CHI-Square | DF | Pr > ChiSq |
|---|---|---|
| 5.6005 | 8 | 0.69 |

TABLE 8

Summary of AHB relations in linear regression models adjusted for age, gender, and BMI

| Response | N | Slope | 95% CI | P-value |
|---|---|---|---|---|
| (1 hr-0 hr) Glucose | 87 | 6.3 | 3.2 to 9.4 | <0.0001 |
| (30 min-0 hr) Glucose | 75 | 4.7 | 2.0 to 7.5 | 0.0009 |
| (1 hr-0 hr) Insulin | 87 | 0.2 | −4.5 to 4.9 | 0.94 |
| (30 min-0 hr) Insulin | 75 | −2.0 | −6.2 to 2.1 | 0.34 |
| (1 hr-0 hr) C-peptide | 87 | 0.2 | −0.1 to 0.4 | 0.21 |
| (30 min-0 hr) C-peptide | 75 | −0.1 | −0.3 to 0.1 | 0.38 |
| Proinsulin | 86 | −0.3 | −1.3 to 0.6 | 0.48 |
| Proinsulin/C-peptide | 86 | −0.2 | −0.6 to 0.2 | 0.32 |

TABLE 9

AHB and LGPC predict change in 1-hour glucose using linear regression model adjusted for age, gender, BMI, and baseline glucose.

Analysis of Variance

| Source | DF | Sum of Squares | Mean Square | F Value | Pr > F |
|---|---|---|---|---|---|
| Model | 6 | 21730 | 3621.68424 | 3.74 | 0.0025 |
| Error | 80 | 77510 | 968.87713 | | |
| Corrected Total | 86 | 99240 | | | |

| | |
|---|---|
| Root MSE | 31.12679 |
| Dependent Mean | 33.79310 |
| Coeff Var | 92.10989 |

TABLE 9-continued

AHB and LGPC predict change in 1-hour glucose using linear regression model adjusted for age, gender, BMI, and baseline glucose.

| | R-Square | 0.2190 |
| | Adj R-Sq | 0.1604 |

Parameter Estimates

| Variable | DF | Parameter Estimate | Standard Error | t Value | Pr > |t| | Variance Inflation | 95% Confidence Limits | |
|---|---|---|---|---|---|---|---|---|
| Intercept | 1 | 27.41477 | 47.28563 | 0.58 | 0.5637 | 0 | −66.68663 | 121.51618 |
| AHB | 1 | 5.53930 | 1.55308 | 3.57 | 0.0006 | 1.07085 | 2.44857 | 8.63003 |
| Age | 1 | 0.02658 | 0.23971 | 0.11 | 0.9120 | 1.04315 | −0.45046 | 0.50362 |
| Male | 1 | 4.92029 | 7.19874 | 0.68 | 0.4963 | 1.15580 | −9.40566 | 19.24624 |
| BMI | 1 | −0.17545 | 0.58160 | −0.30 | 0.7637 | 1.14246 | −1.33288 | 0.98198 |
| GLUC0 | 1 | 0.09669 | 0.48246 | 0.20 | 0.8417 | 1.06759 | −0.86343 | 1.05681 |
| LGPC | 1 | −1.36742 | 0.64695 | −2.11 | 0.0377 | 1.23672 | −2.65489 | −0.07995 |

TABLE 10

AHB and LGPC predict 1-hour glucose ≥ 155 mg/dL using logistic regression model adjusted for age, gender, BMI, and baseline glucose Testing Global Null Hypothesis: BETA = 0

| Test | Chi-Square | DF | Pr > ChiSq |
|---|---|---|---|
| Likelihood Ratio | 18.8646 | 6 | 0.0044 |

Analysis of Maximum Likelihood Estimates

| Parameter | DF | Estimate | Standard Error | Wald Chi-Square | Pr > ChiSq |
|---|---|---|---|---|---|
| Intercept | 1 | −8.3845 | 5.5756 | 2.2613 | 0.1326 |
| AHB | 1 | 0.4641 | 0.1447 | 10.2890 | 0.0013 |
| LGPC | 1 | −0.0680 | 0.0728 | 0.8709 | 0.3507 |
| Age | 1 | 0.0124 | 0.0240 | 0.2680 | 0.6047 |
| Male | 1 | 0.1278 | 0.6948 | 0.0339 | 0.8540 |
| GLUC0 | 1 | 0.0651 | 0.0523 | 1.5477 | 0.2135 |
| BMI | 1 | −0.0230 | 0.0614 | 0.1397 | 0.7086 |

Odds Ratio Estimates

| Effect | Point Estimate | 95% Wald Confidence Limits | |
|---|---|---|---|
| AHB | 1.591 | 1.198 | 2.112 |
| LGPC | 0.934 | 0.810 | 1.078 |
| Age | 1.013 | 0.966 | 1.061 |
| Male | 1.136 | 0.291 | 4.436 |
| GLUC0 | 1.067 | 0.963 | 1.183 |
| BMI | 0.977 | 0.866 | 1.102 |

TABLE 11

Correlations with AHB

| Variable | N | Mean | Std Dev | Minimum | Maximum | Skewness | Kurtosis |
|---|---|---|---|---|---|---|---|
| AHB | 88 | 4.840 | 2.225 | 1.700 | 12.200 | 1.325 | 1.745 |
| FFA0 | 88 | 0.558 | 0.243 | 0.120 | 1.250 | 0.825 | 0.423 |
| CLIX_IR | 88 | 7.642 | 3.472 | 1.880 | 17.200 | 0.926 | 0.318 |
| CLIX_Bcell | 88 | 2.883 | 49.047 | −360.890 | 36.660 | −6.610 | 44.426 |
| hsCRP | 72 | 2.206 | 2.850 | 0.300 | 15.000 | 2.544 | 6.698 |
| Lp_PLA2_DSX | 67 | 140.537 | 40.382 | 54.000 | 249.000 | 0.306 | 0.048 |
| CLIX_Bcell | 86 | 10.177 | 5.885 | 2.260 | 36.660 | 1.577 | 3.846 |

| | FFA0 | CLIX_IR | CLIX_Bcell | hsCRP | Lp_PLA2_DSX |
|---|---|---|---|---|---|
| Pearson Correlation Coefficients Prob > |r| under H0: Rho = 0 | | | | | |
| AHB | 0.45767 | −0.35768 | 0.11665 | 0.10306 | 0.17367 |
| | <.0001 | 0.0006 | 0.2791 | 0.3890 | 0.1599 |
| | 88 | 88 | 88 | 72 | 67 |
| Spearman Correlation Coefficients Prob > |r| under H0: Rho = 0 | | | | | |
| AHB | 0.55913 | −0.39366 | −0.29947 | 0.19634 | 0.11334 |
| | <.0001 | 0.0001 | 0.0046 | 0.0983 | 0.3611 |
| | 88 | 88 | 88 | 72 | 67 |
| Pearson Correlation Coefficients Prob > |r| under H0: Rho = 0 | | | | | |
| AHB | | | −0.31780 | | |
| | | | 0.0029 | | |
| | | | 86 | | |

TABLE 12

Diagnostic metrics for AHB thresholds

| AHB Threshold ≥ [ug/mL] | True Positive | False Positive | Sensitivity | Specificity |
|---|---|---|---|---|
| 1.5 | 15 | 73 | 100.0 | 0.0 |
| 1.8 | 15 | 72 | 100.0 | 1.4 |
| 2.2 | 15 | 70 | 100.0 | 4.1 |
| 2.3 | 15 | 68 | 100.0 | 6.8 |
| 2.4 | 15 | 65 | 100.0 | 11.0 |
| 2.6 | 15 | 64 | 100.0 | 12.3 |
| 2.8 | 15 | 63 | 100.0 | 13.7 |
| 2.9 | 15 | 62 | 100.0 | 15.1 |
| 3.0 | 15 | 60 | 100.0 | 17.8 |
| 3.1 | 15 | 58 | 100.0 | 20.5 |
| 3.2 | 15 | 54 | 100.0 | 26.0 |
| 3.3 | 14 | 52 | 93.3 | 28.8 |
| 3.4 | 14 | 50 | 93.3 | 31.5 |
| 3.5 | 14 | 46 | 93.3 | 37.0 |
| 3.7 | 14 | 44 | 93.3 | 39.7 |
| 3.8 | 13 | 43 | 86.7 | 41.1 |
| 3.9 | 12 | 38 | 80.0 | 47.9 |
| 4.1 | 12 | 35 | 80.0 | 52.1 |
| 4.3 | 12 | 34 | 80.0 | 53.4 |
| 4.4 | 12 | 33 | 80.0 | 54.8 |
| 4.5 | 12 | 31 | 80.0 | 57.5 |
| 4.6 | 11 | 27 | 73.3 | 63.0 |
| 4.7 | 11 | 26 | 73.3 | 64.4 |
| 4.8 | 11 | 23 | 73.3 | 68.5 |
| 5.0 | 10 | 21 | 66.7 | 71.2 |
| 5.1 | 10 | 19 | 66.7 | 74.0 |
| 5.4 | 9 | 18 | 60.0 | 75.3 |
| 5.5 | 9 | 17 | 60.0 | 76.7 |
| 5.6 | 9 | 16 | 60.0 | 78.1 |
| 5.7 | 9 | 15 | 60.0 | 79.5 |
| 6.0 | 9 | 14 | 60.0 | 80.8 |
| 6.1 | 9 | 13 | 60.0 | 82.2 |
| 6.2 | 9 | 11 | 60.0 | 84.9 |
| 6.5 | 8 | 10 | 53.3 | 86.3 |
| 6.6 | 8 | 9 | 53.3 | 87.7 |
| 6.7 | 8 | 7 | 53.3 | 90.4 |
| 6.8 | 8 | 5 | 53.3 | 93.2 |
| 7.1 | 7 | 5 | 46.7 | 93.2 |
| 7.2 | 6 | 4 | 40.0 | 94.5 |
| 7.5 | 6 | 3 | 40.0 | 95.9 |
| 7.7 | 6 | 2 | 40.0 | 97.3 |
| 7.8 | 5 | 2 | 33.3 | 97.3 |
| 9.3 | 5 | 1 | 33.3 | 98.6 |
| 9.5 | 3 | 1 | 20.0 | 98.6 |
| 10.5 | 2 | 1 | 13.3 | 98.6 |
| 11.0 | 1 | 1 | 6.7 | 98.6 |

Case Study:

Patient X is a female aged 40 with normal weight, normal fasting glucose, insulin levels, free fatty acid, and lipid levels at the time of the first serial blood draw for metabolic testing on Feb. 8, 2012. Tests were repeated at 6 time points with the last test being performed on Feb. 27, 2013. Patient has no evidence of metabolic syndrome or Type-2 diabetes but does have a history of late gestational diabetes in 2 pregnancies 8 and 6 years previously which required insulin therapy. Gestational diabetes resolved after delivery and insulin therapy was no longer required. Patient tested negative for anti-GAD antibodies, the classical test for detection of Type 1 diabetes (auto-immune), but patient is positive for Rheumatoid Factor and has been diagnosed with an auto-immune connective tissue disorder (data not shown). However, despite her auto-immune status, tests for biomarkers of inflammation during the course of the year-long follow were unremarkable, however it is possible that auto-immune flares may still skew metabolic test results (tests included Myeloperoxidase, Lp-PLA2, hs-CRP, and Fibrinogen, data not shown).

FIG. 16 shows lipids of Patient X at 6 time points. In FIG. 16A it is indicated that tests were not performed on Feb. 28, 2012 and Apr. 3, 2012.

In FIG. 16B, results from May 2, 2012 (far right column under previous results) and Jul. 10, 2012 (values to left of risk ranges) are shown indicating that the patient is normo-lipidemic.

In FIG. 16C, results from Jan. 28, 2013 (far right column under previous results) and Feb. 27, 2013 (values to left of risk ranges) are shown indicating that the patient is normo-lipidemic.

FIG. 17 shows biomarkers of Glycemic Control, Beta Cell Function, and Insulin Resistance. In FIG. 17A, results from Feb. 28, 2012 (far right column under previous results) and Apr. 3, 2012 (results to left of risk ranges) are shown. Feb. 28, 2012: Fasting blood glucose, FFA, and insulin are all normal. Apr. 3, 2012: Patient was not fasting, so blood glucose and insulin values as well as scores derived therefrom (HOMA IR) cannot be compared to other panels. However, AHB and FFA levels are optimal, and measures of glycemic control such as HbA1c, Fructosamine and Glycation Gap are normal, indicating that blood glucose is well-controlled.

In FIG. 17B, results from May 2, 2012 (far right column under previous results) and Jul. 10, 2012 (values to left of risk ranges) are shown. May 2, 2012: patient is still normo-glycemic, normo-insulinemic and has normal levels of FFA, and AHB. There would be no reason to suspect on the face of these common screening test results that this patient had compromised pancreatic beta cell dysfunction and no evidence of deteriorating condition. Jul. 10, 2012: AHB and FFA levels increase for the first time above the optimal range into the high-risk range. Patient is mildly hypoglycemic (69, close to optimal range of 70 and within experimental error), with optimal insulin levels, and is still normolipidemic. A standard screening test for fasting blood glucose and insulin would not pick up any deterioration in beta cell function or cause a physician to suspect the onset of deterioration of the patient's condition.

In FIG. 17C, results from Jan. 28, 2013 (far right column under previous results) and Feb. 27, 2013 (values to left of risk ranges) are shown. Jan. 28, 2013: AHB is again elevated beyond the threshold of 4.5 into the intermediate risk category while FFA are still in the optimal range. Glucose and insulin are still within the optimal range. Interestingly, a new test for post-prandial glucose index (1,5-anhydroglucitol levels, also known as GlycoMark) is only very slightly elevated over the optimal range (6.1 vs. 6.0). Feb. 26, 2013: AHB levels have increased to a new high of 7.7, and FFA are also again elevated to the high risk range. On this date the patient was hypoglycemic but the estimated daily average glucose was within the optimal range, as was insulin.

Discussion of Data in FIGS. 16 and 17.

These figures collectively show that elevated AHB can be detected at baseline in a patient whose fasting glucose, insulin, and blood lipids are all within normal limits. In FIG. 16C, there are a number of observations worth pointing out. For instance, despite other normal values of glycemic control and the patient being hypoglycemic on Feb. 26, 2013, and though HbA1c is in the optimal range at 5.1, this is the highest value for HbA1c recorded over a 1 year period where all other values fell between 4.7 and 4.9; taken together with the elevated Jan. 28, 2013 intermediate elevation in post-prandial glucose index, the indicate that post-prandial glucose excursions are occurring, possibly causing elevations in glycosylated hemoglobin over the previous months. These results suggest that if an OGTT had been done in the preceding months, abnormal elevations of blood glucose (and blunted secretion of insulin and C-peptide)

would have been detected at 1 hour and/or 30 minutes. Also worth noting: while fasting insulin levels are normal, on the last blood draw date, pro-insulin and c-peptide were abnormally high for the first time, and the pro-insulin: c-peptide ratio was also elevated to the high risk range; this is significant. The appearance of pro-insulin and c-peptide are indicators of beta cell dysfunction; these are released when the pancreas is working to produce insulin as fast as possible in response to high blood sugar (for example in the context of Type 2), or due to deterioration of pancreatic beta cells that then spill immature forms of insulin into the bloodstream (such as in beta cell lysis/damage in auto-immune context of Type 1), or a combination of both conditions. In conditions like this where pancreatic beta cells are being destroyed or exhausted, low and low-normal levels of insulin production do not evidence health, but rather progressing disease. It is in this case that one may observe normal levels of fasting insulin together with lower-than-normal levels of insulin at 1 hour in an OGTT because the pancreatic beta cells "cannot keep up with the demand" in response to elevated blood sugar. Because the first abnormal elevation of AHB and FFA occurred in July 2012 and the first evidence of pancreatic beta cell dysfunction occurred in February 2013, there was an 8-month window from the time elevated AHB signaled a decline in pancreatic beta cell function and the time such dysfunction could be definitively measured by detection of immature forms of insulin in the bloodstream.

The invention described herein would allow for detection of abnormal beta cell function in a patient who otherwise showed no signs of impending beta cell dysfunction by standard diagnostic screening methods, and would have allowed for therapeutic intervention 8 months earlier than conventional diagnostic techniques. It is also worth noting that because this patient was thin and the weight and BMI were lowest for the last test wherein the AHB was highest and the beta cell function had deteriorated the greatest, elevated fasting AHB may a biomarker for the onset of "skinny diabetes", which is a form of adult-onset Type 1 (most commonly observed in Asian populations) requiring exogenous insulin therapy and completely different in etiology to Type 2/metabolic syndrome.

Study No. 3:

In study 3, 217 consecutive nondiabetic subjects underwent a 75 g oral glucose tolerance test (OGTT) and fasting blood collection to evaluate risk of diabetes between March 2012 and May 2013 at several outpatient centers across the US (Madison, Wis.; Jackson, Miss.; Montgomery, Ala.; Charleston, S.C.; Seattle, Wash.; and Salt Lake City, Utah). Clinical indications for testing included obesity, history of first-degree family members with diabetes, and presence of one or more components of the metabolic syndrome, including impaired fasting glucose. Samples were sent by overnight courier to Health Diagnostic Laboratory, Inc. (Richmond, Va.) for measurement of glucose, insulin, metabolites, and other biomarkers. Subjects with detectable anti-GAD antibody (titer >5 IU/ml) were excluded. Patient characteristics and results are shown in table 13.

Insulin resistance (IR) was defined by one or more of the following conditions: fasting glucose ≥100 mg/dL, 2-hour glucose ≥140 mg/dL, HbA1c ≥5.7%, fasting insulin ≥12 µU/mL. Transient hyperglycemia (TH) was defined as 30, 60, or 90-minute glucose ≥140 mg/dL during OGTT. The final study group consisted of 90 IR subjects and 85 healthy subjects with normal levels for all these criteria.

General linear mixed models were used with restricted maximum likelihood (REML) estimation to analyze the mean response profiles for insulin and glucose changes over the 3- or 5-time point 2-hour OGTT. A cubic regression model was fit to the data since the curve's characteristics were known to include two inflection points. The unstructured repeated measures covariance matrix was chosen since it minimized Akaike's Information Criterion (AIC). The insulin response was transformed using the natural transformation to improve the normality and homoscedasticity of the residual errors. To determine if AHB modified the insulin or glucose response, interactions were tested between tertiles of AHB with time, time, and time using F-tests and Wald tests. Interactions were also tested between BMI categories (i.e. normal <25, 25 ≤overweight <30, and obese ≥30 kg/m2) and the cubic time response.

Multivariable logistic regression was used to test the association (i.e. odds ratio) and incremental improvement in discrimination (i.e. c-statistic) of subjects with 1-hour glucose ≥155 mg/dL when AHB was added to age, gender, BMI, fasting glucose, Ln(fasting insulin), Ln(triglycerides), HDL-C, and LDL-C. Fasting insulin and triglycerides were natural logarithm transformed to reduce leverage of extreme observations. When testing the usefulness of a novel biomarker, the American Heart Association recommends reporting the marker's statistical association, discrimination, calibration, and reclassification performance. Hosmer-Lemeshow was used as a measure of model calibration. The reclassification was tested when AHB was added to the fully adjusted logistic regression model with the integrated discrimination improvement (IDI) metric, which can be described as the average increase in sensitivity given no change in specificity. The percentage of subjects who had model probabilities changed in the correct direction (i.e., increased for those with events and decreased for non-events) due to the addition of AHB to the fully adjusted model was tested with the continuous net reclassification index (NRI). SAS® version 9.3 (Cary, N.C.) was used for all analyses, with the critical level set to 0.05 to prescribe statistical significance. Results are shown in table 14.

Figure 18:
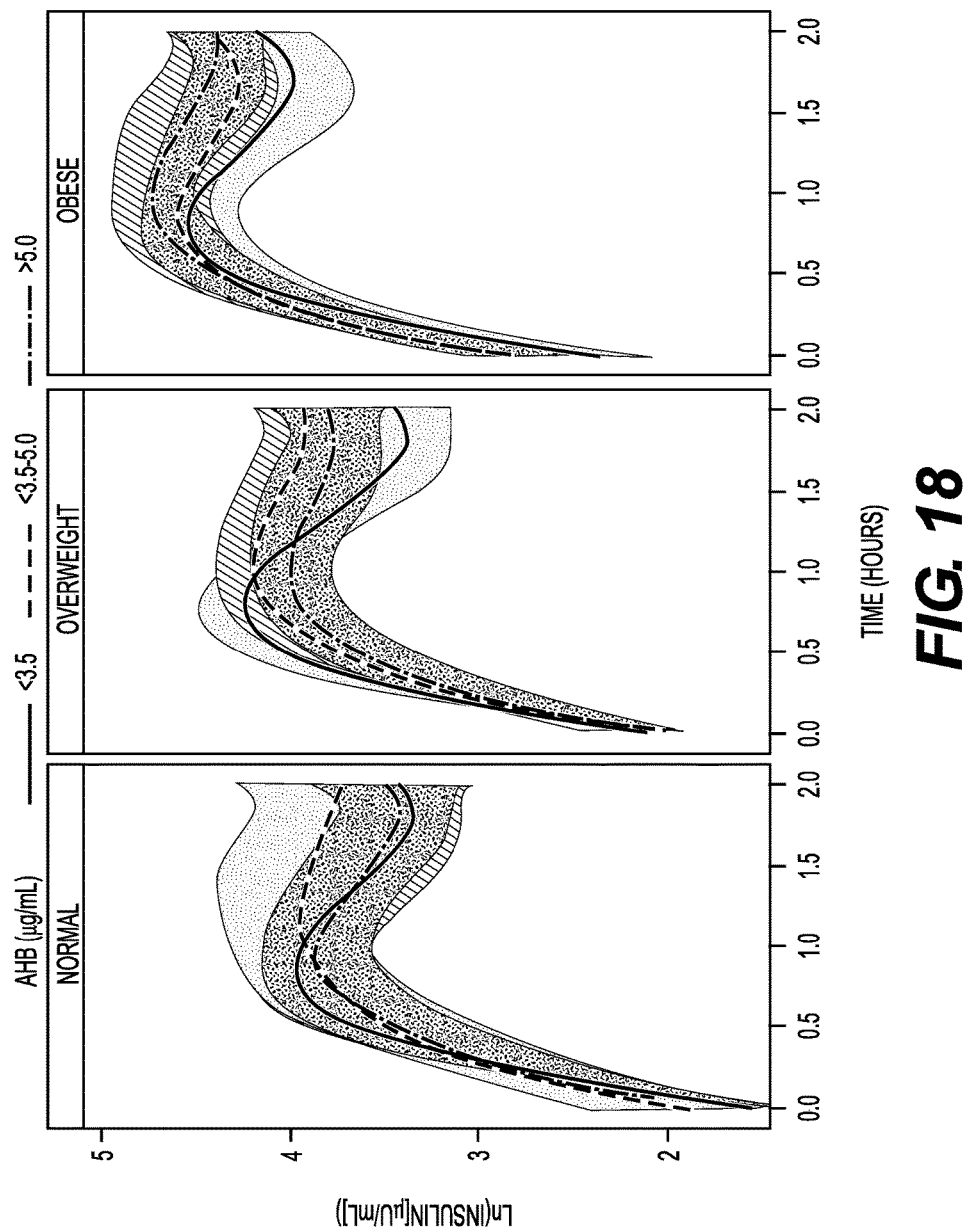
FIG. 18 shows an oral glucose tolerance test (OGTT) insulin response area under the curve (AUC) over time using cubic regression with 95% mean confidence bands for normal, overweight, and obese BMI categories by AHB tertiles.

FIG. 18 shows results from Study 3. OGTT insulin response over time shown with cubic regression and 95% mean confidence bands for normal, overweight, and obese BMI categories by AHB tertiles. In linear mixed models, the $1^{st}$ phase insulin linear slopes were independent of BMI (p=0.16) in models adjusted for age, gender, BMI, fasting glucose, Ln(HbA1c), Ln(triglycerides), HDL-C, and LDL-C. The lowest AHB tertile had a 1st phase linear slope that was 1.67 and 1.33 units greater than the $2^{nd}$ and $3^{rd}$ tertiles, respectively (minimum p=0.0008). The increased slope in the lowest AHB tertiles compared to the higher tertiles shows that the first phase insulin secretion response is suppressed in terms of amount of insulin released and rate of release by increasing amounts of plasma AHB. There was no difference in the $1^{st}$ phase linear slopes between the $2^{nd}$ and $3^{rd}$ AHB tertiles (p=0.39) in fully adjusted models.

Figure 19:
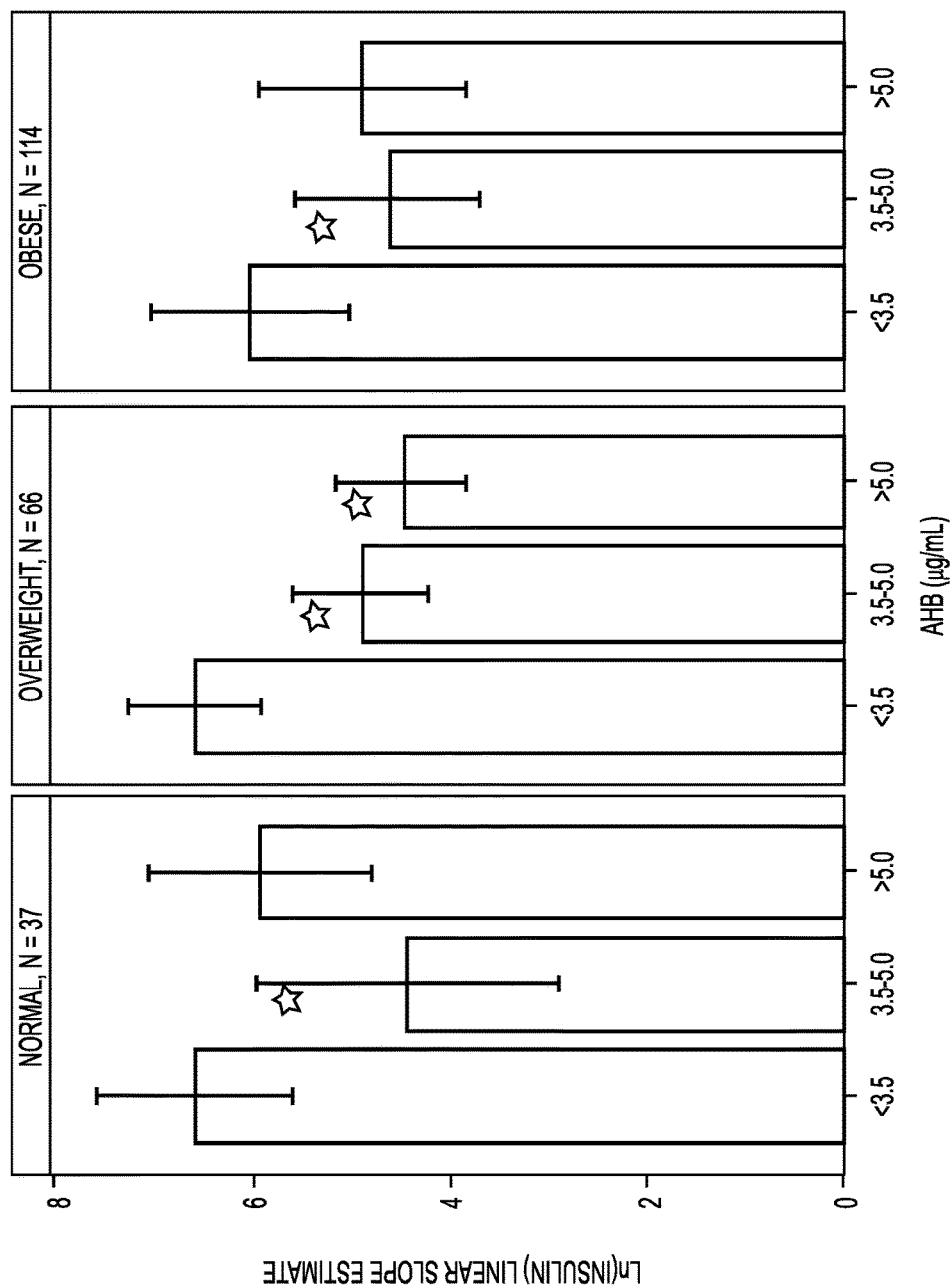
FIG. 19 shows graphs of fitted oral glucose tolerance test (OGTT) insulin response $1^{st}$ phase linear slope estimate with 95% mean confidence intervals for normal, overweight, and obese BMI groups by AHB tertiles.

FIG. 19 Shows fitted OGTT insulin response $1^{st}$ phase linear slope estimate with 95% mean confidence intervals for normal, overweight, and obese BMI groups by AHB tertiles. * p-value <0.05 compared to $1^{st}$ tertile; there were no differences between $2^{nd}$ and $3^{rd}$ tertiles (minimum p-value=0.12).

Figure 20:
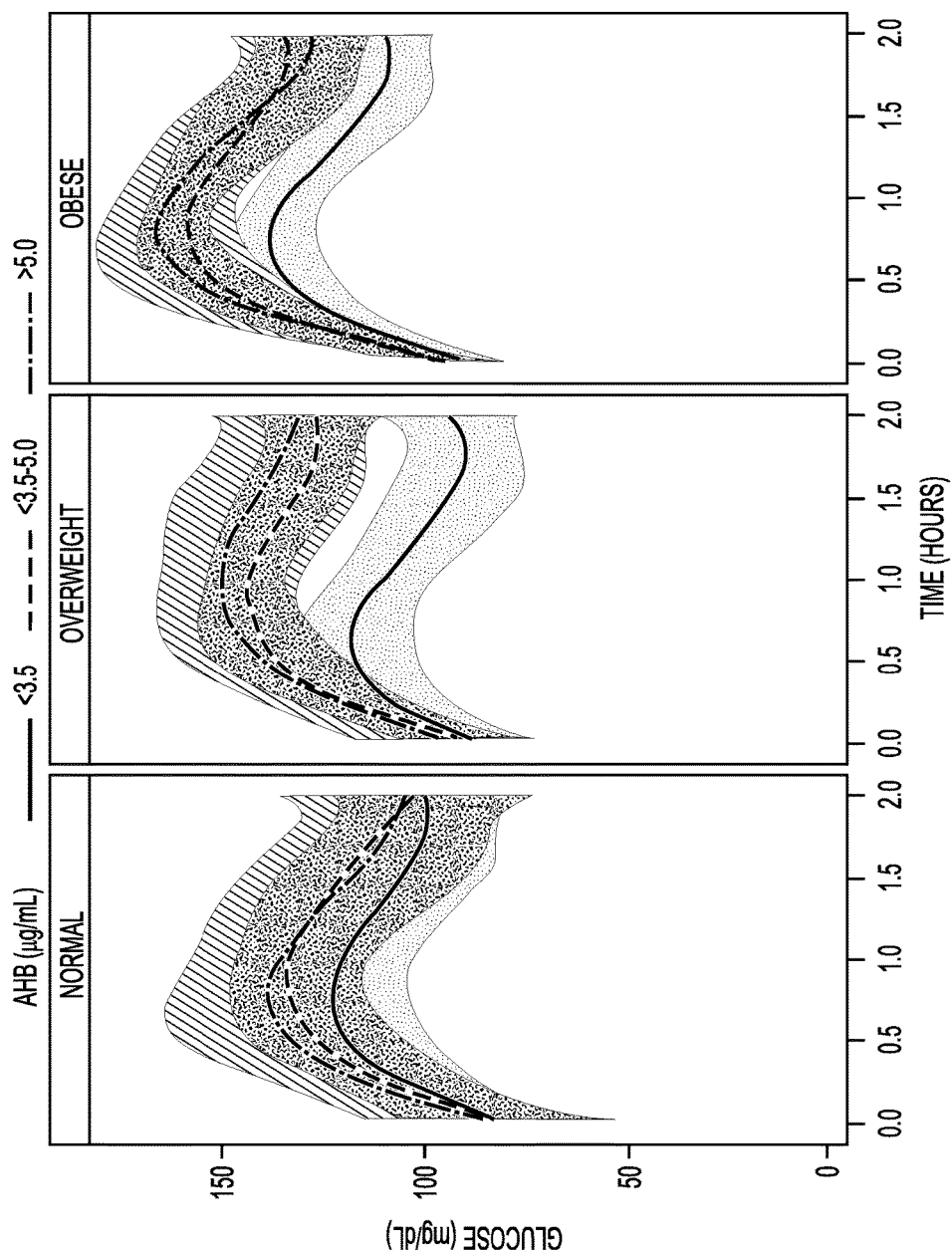
FIG. 20 shows an oral glucose tolerance test (OGTT) glucose response area under the curve (AUC) over time using cubic regression with 95% mean confidence bands for normal, overweight, and obese BMI categories by AHB tertiles.

FIG. 20 shows OGTT glucose response over time shown with cubic regression and 95% mean confidence bands for normal, overweight, and obese BMI categories by AHB tertiles. In linear models, the glucose area under the curve (AUC) was independent of BMI (p=0.55) in models adjusted for age, gender, BMI, fasting insulin, Ln(triglycerides), HDL-C, and LDL-C. The lowest AHB tertile had a glucose AUC that was 32 and 42 units lower than the $2^{nd}$ and $3^{rd}$ tertiles, respectively (minimum p=0.0065), further supporting the decreased first phase insulin response due to beta cell dysfunction as AHB levels increase. The independence of the effect from BMI further underscores the assertion herein that increased levels of AHB are not related to metabolic syndrome/insulin resistance phenomena as currently taught in the literature. There was no difference in the glucose AUC between the $2^{nd}$ and $3^{rd}$ AHB tertiles (p=0.37) in fully adjusted models.

Figure 21:
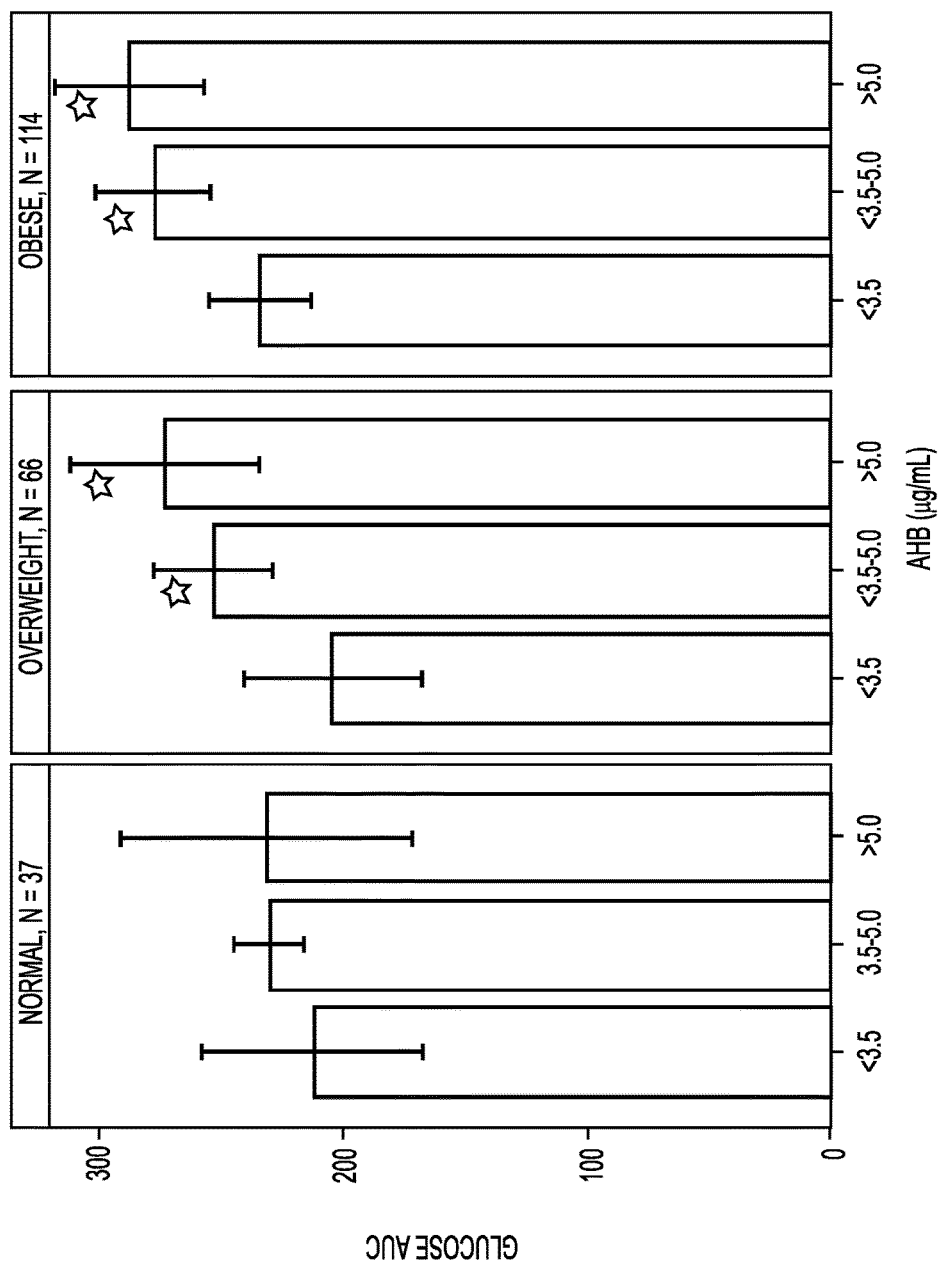
FIG. 21 shows graphs of fitted oral glucose tolerance test (OGTT) glucose response 1st phase linear slope estimate with 95% mean confidence intervals for normal, overweight, and obese BMI groups by AHB tertiles.

FIG. 21 shows OGTT glucose response area under the curve (AUC) shown with 95% mean confidence intervals for normal, overweight and obese BMI groups by AHB tertiles; * p-value <0.05 compared to $1^{st}$ tertile; there were no differences between $2^{nd}$ and $3^{rd}$ tertiles (minimum p-value=0.39). There were no significant differences between corresponding AHB tertiles between BMI groups.

Figure 22:
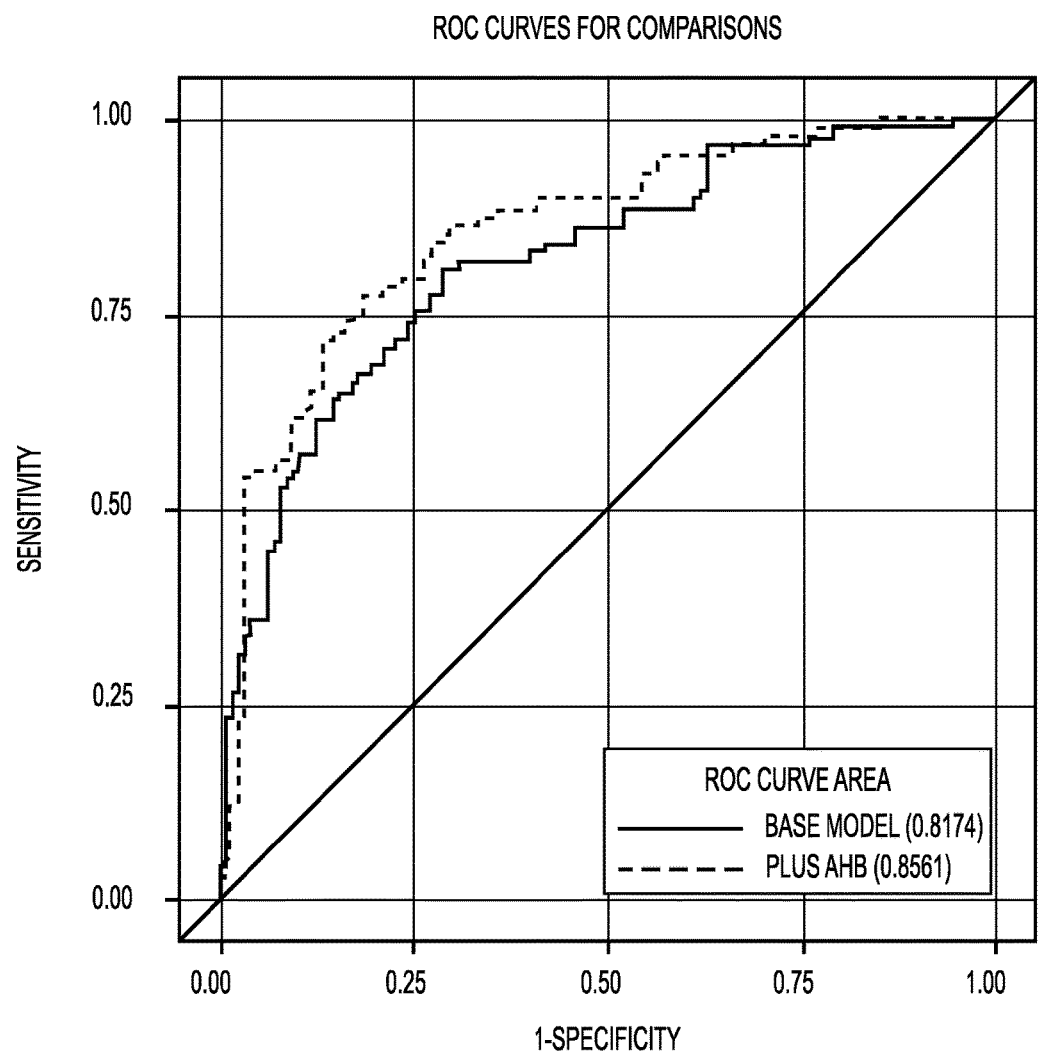
FIG. 22 shows ROC curves for classifying subjects having a 1-hour glucose ≥155 mg/dL during oral glucose tolerance test (OGTT).

FIG. 22 shows ROC curves for classifying subjects having a 1-hour glucose >155 mg/dL during OGTT. The area increased by 0.039 (95% CI: 0.008 to 0.070, p=0.015) when AHB was added to age, gender, BMI, fasting glucose, Ln(fasting insulin), Ln(Triglycerides), HDL-C, and LDL-C in the logistic regression model.

TABLE 13

Patient characteristics grouped by BMI category [kg/m²]

| Variable | BMI < 25 n = 37 | 25 ≤ BMI < 30 n = 66 | BMI ≥ 30 n = 114 | P-value* | Linear Trend P-value |
|---|---|---|---|---|---|
| Age [years] | 53.6 (17.8) | 53.5 (15.0) | 49.3 (13.1) | 0.098 | 0.12 |
| Male: n (%) | 14 (38) | 43 (65) | 39 (34) | 0.0002 | n/a |
| Fasting Glucose [mg/dL] | 84 (9) | 92 (14) | 95 (16) | 0.0003 | <0.0001 |
| 1-hr Glucose [mg/dL] | 130 (55) | 139 (50) | 157 (53) | 0.0083 | 0.0060 |
| 2-hr Glucose [mg/dL] | 103 (53) | 119 (62) | 126 (50) | 0.078 | 0.024 |
| HbA1c† [%] | 5.2 (0.4) | 5.4 (0.5) | 5.6 (0.8) | 0.0010 | 0.0005 |
| Fasting insulin† [uU/mL] | 5.8 (3.6) | 10.2 (7.1) | 19.2 (16.1) | <0.0001 | <0.0001 |
| Triglycerides† [mg/dL] | 78 (44) | 121 (117) | 149 (122) | <0.0001 | <0.0001 |
| HDL Cholesterol [mg/dL] | 68 (20) | 56 (18) | 52 (14) | <0.0001 | <0.0001 |
| LDL Cholesterol [mg/dL] | 93 (34) | 112 (40) | 104 (36) | 0.040 | 0.13 |
| CLIX-IR† | 9.8 (10.2) | 6.5 (3.6) | 4.3 (2.4) | <0.0001 | <0.0001 |
| alpha-hydroxylbutyrate [ug/mL] | 5.4 (3.3) | 5.3 (2.7) | 5.1 (2.2) | 0.77 | 0.56 |
| Anti-GAD Positive: n (%) | 1 (2.7) | 3 (4.6) | 4 (3.5) | 0.88 | n/a |
| Insulin Resistant: n (%) | 11 (30) | 32 (48) | 78 (68) | <0.0001 | n/a |
| 1-hr Glucose ≥ 155 [mg/dL]: n (%) | 11 (30) | 19 (29) | 58 (51) | 0.0049 | n/a |
| Transient Hyperglycemia: (n (%) | 17 (46) | 34 (52) | 77 (68) | 0.023 | n/a |

Data are mean (SD) unless stated otherwise:
*One-way ANOVA and Chi-squared test for continuous and categorical data, respectively;
†Used natural logarithm transformation for improved normality and homoscedasticity of residual errors in linear models.

TABLE 14

ROC curve comparisons for classifying subjects having a 1-hour glucose > 155 mg/dL during OGTT (Study #3)

| | AUC (c-statistic) | | | P-value Difference |
|---|---|---|---|---|
| | Without AHB | With AHB | AUC Difference (95% CI) | |
| Model 1: Age, Gender | 0.632 | 0.739 | 0.107 (0.043 to 0.172) | 0.0011 |
| Model 1 + BMI | 0.702 | 0.775 | 0.073 (0.021 to 0.126) | 0.0066 |
| Model 1 + fasting glucose | 0.786 | 0.836 | 0.050 (0.014 to 0.086) | 0.0069 |
| Model 1 + Ln (HbA1c) | 0.753 | 0.807 | 0.054 (0.011 to 0.098) | 0.014 |
| Model 1 + Ln (fasting insulin) | 0.751 | 0.821 | 0.071 (0.026 to 0.115) | 0.0019 |
| Model 1 + Ln (trigs), HDL-C, LDL-C | 0.727 | 0.787 | 0.060 (0.015 to 0.106) | 0.0098 |
| All covariates | 0.821 | 0.857 | 0.037 (0.005 to 0.069) | 0.025 |

The area increased by 0.037 (95% CI: 0.005 to 0.069, p = 0.025) when AHB was added to age, gender, BMI, fasting glucose, Ln(HbA1c), Ln(fasting insulin), Ln(Triglycerides), HDL-C, and LDL-C in the logistic regression model.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating a patient determined to be at risk for developing occult pancreatic beta cell dysfunction, the method comprising:
   a. measuring a level of alpha-hydroxybutyrate (AHB) in a single fasting baseline biological sample of the patient, wherein AHB is the sole biomarker used to determine whether the patient is at risk for developing occult pancreatic beta cell dysfunction;
   b. comparing the level of AHB in the single fasting baseline biological sample to a reference AHB level;
   c. determining an increased likelihood of an impaired first phase insulin secretion response, based on the comparison of step (b); and
   d. administering to the patient a diabetes therapy if the level of AHB is greater than 4.5 µg/mL;
   wherein the patient is normoglycemic, normoinsulinemic and/or non-dyslipidemic, and wherein the patient shows no apparent beta cell dysfunction, as detected by conventional diagnostic techniques.

2. The method of claim 1, further comprising measuring one or more additional biomarkers in one or more biological samples of the patient.

3. The method of claim 2, wherein the one or more biomarkers are selected from the group consisting of glucose, insulin, HDL, HDL-c, triglycerides, LDL, LDL-c, C-peptide, 1,5-anhydroglucitol, and pro-insulin.

4. The method of claim 2, wherein the one or more biomarkers are selected from the group consisting of autoantibodies present in type-1 diabetes; viral nucleic acids; biomarkers to autoimmune diseases; viral DNAs, viral RNAs and antibodies to viral capsid proteins for members of the Enterovirus family.

5. The method of claim 2, wherein the one or more biomarkers are selected from the group consisting of glucose, insulin, anti-islet cell cytoplasmic (anti-ICA) antibodies, glutamic acid decarboxylase (anti-GAD) autoantibodies, 1,5-anhydroglucitol, hemoglobin (Hb) A1c, fructosamine, mannose, D-mannose, mannose-binding lectin (MBL) amount, mannose binding lectin (MBL) activity, 1,5-anhydroglucitol (1,5 AG), glycation gap (glycosylation gap), serum amylase, c-peptide, intact pro-insulin, leptin, adiponectin, leptin/adiponectin ratio, ferritin, free fatty acids, lipoprotein-associated phospholipase A2 (Lp-PLA2), fibrinogen, myeloperoxidase, cystatin C, homocysteine, F2-isoprostanes, α-hydroxybutyrate (AHB), linoleoyl glycerophosphocholine (L-GPC), oleic acid (OA), analytes associated with IR score, analytes associated with HOMA (Homeostasis Model Assessment) IR score, analytes associated with CLIX score, gamma-glutamic transferase (GGT), uric acid, vitamin B12, homocysteine, 25-hydroxyvitamin D, TSH, estimated glomerular filtration rate (eGFR), and serum creatinine.

6. The method of claim 5, further comprising measuring the anti-ICA or anti-GAD auto-antibodies biomarkers in the biological sample, wherein a positive reaction to one of the biomarkers indicates an increased risk of occult pancreatic beta cell dysfunction.

7. The method of claim 2, wherein the one or more biomarkers are selected from the group consisting of body mass index (BMI); free fatty acids; low density lipoprotein particle number (LDL-P); LDL-cholesterol (LDL-C); triglyceride; high density lipoprotein particle number (HDL-P); high density lipoprotein-cholesterol (HDL-C); high sensitivity C-reactive protein (hs-CRP); remnant-like lipoproteins (RLPs); RLP-(cholesterol measures); apolipoprotein A-1; HDL2; ApoB:ApoA-1 ratio; Lp(a) mass; Lp(a) cholesterol; large VLDL-P; small LDL-P; large HDL-P; VLDL-size; LDL size; HDL size; LP-IR score; apolipoprotein A-1 (ApoA-1); apolipoprotein B (ApoB); apolipoprotein C (ApoC); apolipoprotein E (ApoE); and ApoE subspecies, variations, fragments, PTMs and isoforms thereof.

8. The method of claim 2, wherein the one or more biomarkers are selected from the group consisting of campesterol, sitosterol (β-sitosterol), cholestanol, desmosterol, lathosterol, and squalene.

9. The method of claim 2, wherein the one or more biomarkers are biomarkers for coagulation or dyslipidemia.

10. The method of claim 1, wherein the comparison of step (b) also indicates that said patient is at risk of a diabetic condition selected from the group consisting of cardiodiabetes, gestational diabetes, latent autoimmune diabetes of adults (LADA), mixed phenotype diabetic conditions, and atypical forms of type 1 diabetes.

11. The method of claim 10, wherein the atypical form of type 1 diabetes is insulin autoimmune syndrome (IAS).

12. The method of claim 1, wherein the comparison of step (b) is used to predict an increased likelihood of a requirement for exogenous insulin supplementation.

13. The method of claim 1, wherein the patient is at risk for a cardiodiabetic disease associated with occult pancreatic beta cell dysfunction.

14. The method of claim 13, wherein the cardiodiabetic disease is selected from the group consisting of retinopathy, neuropathy, nephropathy, atherosclerosis, stroke, myocardial infarction, gestational diabetes, pre-term labor, and the birth of high birth-weight infants.

15. The method of claim 1, further comprising effectuating a therapy guidance if the AHB level is greater than 4.5 µg/mL.

16. The method of claim 15, wherein the therapy guidance involves one of more of the following: performing a confirmatory OGTT and/or additional diagnostic testing, prescribing a drug therapy, increasing monitoring frequency of patient condition, and recommending appropriate risk-reduction therapy and lifestyle choices based on the determination in step (d) of claim 1.

17. The method of claim 16, wherein the lifestyle choices involve changes in diet and nutrition, changes in exercise, smoking elimination or a combination thereof.

18. The method of claim 15, wherein the therapy guidance involves administration of antioxidants, administration of anti-coagulants, administration of anti-dyslipidemic drugs, avoidance of drugs or agents known to damage pancreatic cells; discontinued administration of current drug therapy, administration of agents specific for post-prandial hyperglycemia (e.g. cycloset), administration of drugs that enhance, and/or augment, and/or spare pancreatic beta cell function, administration of an anti-viral agent, an immunosuppressant or insulin or an insulin analog or combinations thereof.

19. The method of claim 15, wherein the therapy guidance involves one or more of the following: increased frequency of physician's follow-up, referral for oral glucose tolerance test (OGTT) and/or CLIX test, repetition of tests for monitoring disease progression, patient referral for comprehensive testing for type I diabetes; testing for auto-antibodies to pancreatic cell antigens, other biomarkers for autoimmune diseases, viral DNA/RNA and/or antibodies to viral capsid proteins for Enterovirus family members or combinations thereof.

20. The method of claim 1, wherein the biological sample is selected from the group consisting of a blood component, saliva and urine.

21. A method of treating a patient determined to be at risk for developing occult pancreatic beta cell dysfunction in a patient, comprising administering a diabetes therapy to a normoglycemic, normoinsulinemic and/or non-dyslipidemic patient, wherein the patient is determined to have a level of AHB greater than 4.5 µg/mL; wherein AHB was the sole biomarker used to determine whether the patient is at risk for developing occult pancreatic beta cell dysfunction; and wherein the patient shows no apparent beta cell dysfunction, as detected by conventional diagnostic techniques.

* * * * *